US008672997B2

(12) United States Patent
Drasler et al.

(10) Patent No.: US 8,672,997 B2
(45) Date of Patent: Mar. 18, 2014

(54) VALVE WITH SINUS

(75) Inventors: William J. Drasler, Minnetonka, MN (US); Mark L. Jensen, Greenfield, MN (US); Jason P. Hill, Brooklyn Park, MN (US); David J. Sogard, Edina, MN (US); Patrick A. Haverkost, Brooklyn Center, MN (US); Susan M. Shoemaker, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/454,778

(22) Filed: Apr. 24, 2012

(65) Prior Publication Data
US 2012/0209378 A1    Aug. 16, 2012

Related U.S. Application Data

(63) Continuation of application No. 11/652,299, filed on Jan. 11, 2007, now abandoned, which is a continuation-in-part of application No. 11/232,403, filed on Sep. 21, 2005, now Pat. No. 7,569,071.

(51) Int. Cl.
A61F 2/24     (2006.01)

(52) U.S. Cl.
USPC ........ 623/1.24; 623/1.3; 623/2.16; 623/2.178

(58) Field of Classification Search
USPC ............ 623/1.24, 1.26, 2.1–2.19, 2.42, 1.3
See application file for complete search history.

(56) References Cited

U.S. PATENT DOCUMENTS

| 3,671,979 | A |   | 6/1972  | Moulopoulos |
| 4,222,126 | A | * | 9/1980  | Boretos et al. ............... 623/2.19 |
| 4,291,420 | A |   | 9/1981  | Reul |
| 4,787,901 | A |   | 11/1988 | Baykut |
| 4,872,874 | A |   | 10/1989 | Taheri |
| 4,935,030 | A |   | 6/1990  | Alonso |
| 4,994,077 | A |   | 2/1991  | Dobben |
| 5,002,567 | A |   | 3/1991  | Bona et al. |
| 5,141,491 | A |   | 8/1992  | Bowald |
| 5,163,953 | A |   | 11/1992 | Vince |
| 5,219,355 | A |   | 6/1993  | Parodi et al. |
| 5,254,127 | A |   | 10/1993 | Wholey et al. |
| 5,327,774 | A |   | 7/1994  | Nguyen et al. |
| 5,332,402 | A |   | 7/1994  | Teitelbaum |
| 5,370,685 | A |   | 12/1994 | Stevens |
| 5,415,667 | A | * | 5/1995  | Frater ........................ 623/2.11 |
| 5,441,552 | A |   | 8/1995  | DeLillo |
| 5,469,868 | A |   | 11/1995 | Reger |
| 5,480,423 | A |   | 1/1996  | Ravenscroft et al. |
| 5,500,014 | A |   | 3/1996  | Quijano et al. |
| 5,545,214 | A |   | 8/1996  | Stevens |
| 5,554,185 | A |   | 9/1996  | Block et al. |
| 5,643,208 | A |   | 7/1997  | Parodi |

(Continued)

FOREIGN PATENT DOCUMENTS

| EP | 0380666 | 8/1990 |
| EP | 0466518 | 1/1992 |

(Continued)

Primary Examiner — David Isabella
Assistant Examiner — Suba Ganesan
(74) Attorney, Agent, or Firm — Vidas, Arrett & Steinkraus, P.A.

(57) ABSTRACT

A valve with a structural member and valve leaflets that provide a sinus.

20 Claims, 15 Drawing Sheets

(56) References Cited

U.S. PATENT DOCUMENTS

| | | |
|---|---|---|
| 5,693,087 A | 12/1997 | Parodi |
| 5,713,953 A | 2/1998 | Vallana et al. |
| 5,716,370 A | 2/1998 | Williamson, IV et al. |
| 5,735,859 A | 4/1998 | Fischell et al. |
| 5,741,326 A | 4/1998 | Solovay |
| 5,741,333 A | 4/1998 | Frid |
| 5,800,506 A | 9/1998 | Perouse |
| 5,824,061 A | 10/1998 | Quijano et al. |
| 5,879,320 A | 3/1999 | Cazenave |
| 5,895,419 A | 4/1999 | Tweden et al. |
| 5,910,170 A | 6/1999 | Reimink et al. |
| 6,010,531 A | 1/2000 | Donlon et al. |
| 6,042,607 A | 3/2000 | Williamson, IV et al. |
| 6,139,575 A | 10/2000 | Shu et al. |
| 6,287,334 B1 | 9/2001 | Moll et al. |
| 6,312,447 B1 | 11/2001 | Grimes |
| 6,355,030 B1 | 3/2002 | Aldrich et al. |
| 6,402,780 B2 | 6/2002 | Williamson, IV et al. |
| 6,419,696 B1 | 7/2002 | Ortiz et al. |
| 6,425,916 B1 | 7/2002 | Garrison et al. |
| 6,440,164 B1 | 8/2002 | DiMatteo et al. |
| 6,451,054 B1 | 9/2002 | Stevens |
| 6,454,799 B1 | 9/2002 | Schreck |
| 6,461,366 B1 | 10/2002 | Seguin |
| 6,503,272 B2 | 1/2003 | Duerig et al. |
| 6,508,833 B2 | 1/2003 | Pavcnik et al. |
| 6,564,805 B2 | 5/2003 | Garrison et al. |
| 6,569,196 B1 | 5/2003 | Vesely |
| 6,602,286 B1 | 8/2003 | Strecker |
| 6,629,534 B1 | 10/2003 | St. Goar et al. |
| 6,635,085 B1 | 10/2003 | Caffey et al. |
| 6,666,885 B2 | 12/2003 | Moe |
| 6,666,886 B1 | 12/2003 | Tranquillo et al. |
| 6,669,725 B2 | 12/2003 | Scott |
| 6,673,109 B2 | 1/2004 | Cox |
| 6,676,698 B2 | 1/2004 | McGuckin, Jr. et al. |
| 6,676,702 B2 | 1/2004 | Mathis |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,692,512 B2 | 2/2004 | Jang |
| 6,695,866 B1 | 2/2004 | Kuehn et al. |
| 6,695,878 B2 | 2/2004 | McGuckin, Jr. et al. |
| 6,709,456 B2 | 3/2004 | Langberg et al. |
| 6,709,457 B1 | 3/2004 | Otte et al. |
| 6,716,241 B2 | 4/2004 | Wilder et al. |
| 6,716,244 B2 | 4/2004 | Klaco |
| 6,719,767 B1 | 4/2004 | Kimblad |
| 6,719,784 B2 | 4/2004 | Henderson |
| 6,719,786 B2 | 4/2004 | Ryan et al. |
| 6,719,787 B2 | 4/2004 | Cox |
| 6,719,788 B2 | 4/2004 | Cox |
| 6,719,789 B2 | 4/2004 | Cox |
| 6,719,790 B2 | 4/2004 | Brendzel et al. |
| 6,723,038 B1 | 4/2004 | Schroeder et al. |
| 6,723,122 B2 | 4/2004 | Yang et al. |
| 6,723,123 B1 | 4/2004 | Kazatchkov et al. |
| 6,726,715 B2 | 4/2004 | Sutherland |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,730,122 B1 | 5/2004 | Pan et al. |
| 6,736,845 B2 | 5/2004 | Marquez et al. |
| 6,736,846 B2 | 5/2004 | Cox |
| 6,749,630 B2 | 6/2004 | McCarthy et al. |
| 6,752,813 B2 | 6/2004 | Goldfarb et al. |
| 6,752,828 B2 | 6/2004 | Thornton |
| 6,755,857 B2 | 6/2004 | Peterson et al. |
| 6,761,734 B2 | 7/2004 | Suhr |
| 6,761,735 B2 | 7/2004 | Eberhardt et al. |
| 6,764,494 B2 | 7/2004 | Menz et al. |
| 6,764,508 B1 | 7/2004 | Roehe et al. |
| 6,764,509 B2 | 7/2004 | Chinn et al. |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,770,083 B2 | 8/2004 | Seguin |
| 6,780,200 B2 | 8/2004 | Jansen |
| 6,786,924 B2 | 9/2004 | Ryan et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,231 B2 | 9/2004 | Liddicoat et al. |
| 6,793,673 B2 | 9/2004 | Kowalsky et al. |
| 6,797,000 B2 | 9/2004 | Simpson et al. |
| 6,797,001 B2 | 9/2004 | Mathis et al. |
| 6,797,002 B2 | 9/2004 | Spence et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,830,584 B1 | 12/2004 | Seguin |
| 6,830,585 B1 | 12/2004 | Artof et al. |
| 6,837,902 B2 | 1/2005 | Nguyen et al. |
| 6,840,246 B2 | 1/2005 | Downing |
| 6,840,957 B2 | 1/2005 | DiMatteo et al. |
| 6,846,324 B2 | 1/2005 | Stobie |
| 6,846,325 B2 | 1/2005 | Liddicoat |
| 6,858,039 B2 | 2/2005 | McCarthy |
| 6,869,444 B2 | 3/2005 | Gabbay |
| 6,872,226 B2 | 3/2005 | Cali et al. |
| 6,875,224 B2 | 4/2005 | Grimes |
| 6,875,230 B1 | 4/2005 | Morita et al. |
| 6,875,231 B2 | 4/2005 | Anduiza et al. |
| 6,881,199 B2 | 4/2005 | Wilk et al. |
| 6,881,224 B2 | 4/2005 | Kruse et al. |
| 6,883,522 B2 | 4/2005 | Spence et al. |
| 6,890,352 B1 | 5/2005 | Lentell |
| 6,890,353 B2 | 5/2005 | Cohn et al. |
| 6,893,459 B1 | 5/2005 | Macoviak |
| 6,893,460 B2 | 5/2005 | Spenser et al. |
| 6,896,700 B2 | 5/2005 | Lu et al. |
| 6,902,576 B2 | 6/2005 | Drasler et al. |
| 6,908,478 B2 | 6/2005 | Alferness et al. |
| 6,908,481 B2 | 6/2005 | Cribier |
| 6,911,043 B2 | 6/2005 | Myers et al. |
| 6,913,608 B2 | 7/2005 | Liddicoat et al. |
| 6,916,338 B2 | 7/2005 | Speziali |
| 6,918,917 B1 | 7/2005 | Nguyen et al. |
| 6,921,407 B2 | 7/2005 | Nguyen et al. |
| 6,921,811 B2 | 7/2005 | Zamora et al. |
| 6,926,715 B1 | 8/2005 | Hauck et al. |
| 6,926,730 B1 | 8/2005 | Nguyen et al. |
| 6,929,653 B2 | 8/2005 | Strecter |
| 6,932,838 B2 | 8/2005 | Schwartz et al. |
| 6,936,067 B2 | 8/2005 | Buchanan |
| 6,939,359 B2 | 9/2005 | Tu et al. |
| 6,942,694 B2 | 9/2005 | Liddicoat et al. |
| 6,945,957 B2 | 9/2005 | Freyman |
| 6,945,978 B1 | 9/2005 | Hyde |
| 6,945,996 B2 | 9/2005 | Sedransk |
| 6,945,997 B2 | 9/2005 | Huynh et al. |
| 6,949,122 B2 | 9/2005 | Adams et al. |
| 6,951,571 B1 | 10/2005 | Srivastava |
| 6,951,573 B1 | 10/2005 | Dilling |
| 6,953,332 B1 | 10/2005 | Kurk et al. |
| 6,955,689 B2 | 10/2005 | Ryan et al. |
| 6,958,076 B2 | 10/2005 | Acosta et al. |
| 6,962,605 B2 | 11/2005 | Cosgrove et al. |
| 6,964,682 B2 | 11/2005 | Nguyen-Thien-Nhon et al. |
| 6,964,683 B2 | 11/2005 | Kowalsky et al. |
| 6,964,684 B2 | 11/2005 | Ortiz et al. |
| 6,966,925 B2 | 11/2005 | Stobie |
| 6,966,926 B2 | 11/2005 | Mathis |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,976,995 B2 | 12/2005 | Mathis et al. |
| 6,979,350 B2 | 12/2005 | Moll et al. |
| 6,986,775 B2 | 1/2006 | Morales et al. |
| 6,989,027 B2 | 1/2006 | Allen et al. |

(56) References Cited

U.S. PATENT DOCUMENTS

| | | |
|---|---|---|
| 6,989,028 B2 | 1/2006 | Lashinski et al. |
| 6,997,950 B2 | 2/2006 | Chawla |
| 6,997,951 B2 | 2/2006 | Solem et al. |
| 7,004,176 B2 | 2/2006 | Lau |
| 7,007,396 B2 | 3/2006 | Rudko et al. |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,018,407 B1 | 3/2006 | Wright et al. |
| 7,018,408 B2 | 3/2006 | Bailey et al. |
| 7,022,134 B1 | 4/2006 | Quijano et al. |
| 7,025,780 B2 | 4/2006 | Gabbay |
| 7,033,390 B2 | 4/2006 | Johnson et al. |
| 7,037,333 B2 | 5/2006 | Myers et al. |
| 7,037,334 B1 | 5/2006 | Hlavka et al. |
| 7,041,128 B2 | 5/2006 | Mcguckin, Jr. et al. |
| 7,041,132 B2 | 5/2006 | Quijano et al. |
| 7,044,966 B2 | 5/2006 | Svanidze et al. |
| 7,044,967 B1 | 5/2006 | Solem et al. |
| 7,048,754 B2 | 5/2006 | Martin et al. |
| 7,048,757 B2 | 5/2006 | Shaknovich |
| 7,052,487 B2 | 5/2006 | Cohn et al. |
| 7,052,507 B2 | 5/2006 | Wakuda et al. |
| 7,063,722 B2 | 6/2006 | Marquez |
| 7,066,954 B2 | 6/2006 | Ryan |
| 7,070,616 B2 | 7/2006 | Majercak et al. |
| 7,070,618 B2 | 7/2006 | Streeter |
| 7,077,862 B2 | 7/2006 | Vidlund et al. |
| 7,081,131 B2 | 7/2006 | Thornton |
| 7,087,064 B1 | 8/2006 | Hyde |
| 7,089,051 B2 | 8/2006 | Javerud et al. |
| 7,090,695 B2 | 8/2006 | Solem et al. |
| 7,637,937 B2 | 12/2009 | Case |
| 2001/0010017 A1* | 7/2001 | Letac et al. .................. 623/2.11 |
| 2001/0011187 A1 | 8/2001 | Pavcnik et al. |
| 2002/0013571 A1 | 1/2002 | Goldfarb et al. |
| 2002/0026216 A1 | 2/2002 | Grimes |
| 2002/0082630 A1 | 6/2002 | Menz et al. |
| 2002/0123802 A1 | 9/2002 | Snyders |
| 2002/0151970 A1 | 10/2002 | Garrison et al. |
| 2002/0173842 A1* | 11/2002 | Buchanan .................... 623/2.14 |
| 2002/0178570 A1 | 12/2002 | Sogard |
| 2002/0183835 A1 | 12/2002 | Taylor et al. |
| 2002/0183838 A1 | 12/2002 | Liddicoat et al. |
| 2002/0198594 A1 | 12/2002 | Schreck |
| 2003/0050694 A1 | 3/2003 | Yang et al. |
| 2003/0130729 A1 | 7/2003 | Paniagua et al. |
| 2003/0163194 A1 | 8/2003 | Quijano et al. |
| 2003/0167071 A1 | 9/2003 | Martin |
| 2003/0171806 A1 | 9/2003 | Mathis et al. |
| 2003/0199975 A1 | 10/2003 | Gabbay |
| 2003/0229394 A1 | 12/2003 | Ogle et al. |
| 2003/0229395 A1 | 12/2003 | Cox |
| 2003/0233142 A1 | 12/2003 | Morales et al. |
| 2003/0236568 A1 | 12/2003 | Hojeibane et al. |
| 2003/0236569 A1 | 12/2003 | Mathis et al. |
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015230 A1 | 1/2004 | Moll et al. |
| 2004/0015232 A1 | 1/2004 | Shu et al. |
| 2004/0015233 A1 | 1/2004 | Jansen |
| 2004/0019374 A1 | 1/2004 | Hojeibane et al. |
| 2004/0019377 A1 | 1/2004 | Taylor et al. |
| 2004/0019378 A1 | 1/2004 | Hlavka et al. |
| 2004/0024447 A1 | 2/2004 | Haverich |
| 2004/0024451 A1 | 2/2004 | Johnson et al. |
| 2004/0024452 A1 | 2/2004 | Kruse et al. |
| 2004/0030321 A1 | 2/2004 | Fangrow, Jr. |
| 2004/0030381 A1 | 2/2004 | Shu |
| 2004/0030382 A1 | 2/2004 | St. Goar et al. |
| 2004/0030405 A1 | 2/2004 | Carpentier et al. |
| 2004/0034380 A1 | 2/2004 | Woolfson et al. |
| 2004/0034411 A1 | 2/2004 | Quijano et al. |
| 2004/0039436 A1 | 2/2004 | Spenser et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0044403 A1 | 3/2004 | Bischoff et al. |
| 2004/0049207 A1 | 3/2004 | Goldfarb et al. |
| 2004/0049211 A1 | 3/2004 | Tremulis et al. |
| 2004/0049266 A1 | 3/2004 | Anduiza et al. |
| 2004/0059351 A1 | 3/2004 | Eigler et al. |
| 2004/0059411 A1 | 3/2004 | Strecker |
| 2004/0059412 A1 | 3/2004 | Lytle, IV et al. |
| 2004/0060161 A1 | 4/2004 | Leal et al. |
| 2004/0073301 A1 | 4/2004 | Donlon et al. |
| 2004/0073302 A1 | 4/2004 | Rourke et al. |
| 2004/0078072 A1 | 4/2004 | Tu et al. |
| 2004/0078074 A1 | 4/2004 | Anderson et al. |
| 2004/0082910 A1 | 4/2004 | Constantz et al. |
| 2004/0082923 A1 | 4/2004 | Field |
| 2004/0082991 A1 | 4/2004 | Nguyen et al. |
| 2004/0087975 A1 | 5/2004 | Lucatero et al. |
| 2004/0088045 A1 | 5/2004 | Cox |
| 2004/0088046 A1 | 5/2004 | Speziali |
| 2004/0092858 A1 | 5/2004 | Wilson et al. |
| 2004/0093060 A1 | 5/2004 | Seguin et al. |
| 2004/0093070 A1 | 5/2004 | Hojeibane et al. |
| 2004/0093080 A1 | 5/2004 | Helmus |
| 2004/0097979 A1 | 5/2004 | Svanidze et al. |
| 2004/0098098 A1 | 5/2004 | McGuckin, Jr. et al. |
| 2004/0098112 A1 | 5/2004 | DiMatteo et al. |
| 2004/0102839 A1 | 5/2004 | Cohn et al. |
| 2004/0102840 A1 | 5/2004 | Solem et al. |
| 2004/0102842 A1 | 5/2004 | Jansen |
| 2004/0106976 A1 | 6/2004 | Bailey et al. |
| 2004/0106990 A1 | 6/2004 | Spence et al. |
| 2004/0106991 A1 | 6/2004 | Hopkins et al. |
| 2004/0111096 A1 | 6/2004 | Tu et al. |
| 2004/0117009 A1 | 6/2004 | Cali et al. |
| 2004/0122448 A1 | 6/2004 | Levine |
| 2004/0122512 A1 | 6/2004 | Navia et al. |
| 2004/0122513 A1 | 6/2004 | Navia et al. |
| 2004/0122514 A1 | 6/2004 | Fogarty et al. |
| 2004/0122515 A1 | 6/2004 | Chu |
| 2004/0122516 A1 | 6/2004 | Fogarty et al. |
| 2004/0127979 A1 | 7/2004 | Wilson et al. |
| 2004/0127980 A1 | 7/2004 | Kowalsky et al. |
| 2004/0127981 A1 | 7/2004 | Randert et al. |
| 2004/0127982 A1 | 7/2004 | Machold et al. |
| 2004/0133220 A1 | 7/2004 | Lashinski et al. |
| 2004/0133267 A1 | 7/2004 | Lane |
| 2004/0133273 A1 | 7/2004 | Cox |
| 2004/0138742 A1 | 7/2004 | Myers et al. |
| 2004/0138743 A1 | 7/2004 | Myers et al. |
| 2004/0138744 A1 | 7/2004 | Lashinski et al. |
| 2004/0138745 A1 | 7/2004 | Macoviak et al. |
| 2004/0148018 A1 | 7/2004 | Carpentier et al. |
| 2004/0148019 A1 | 7/2004 | Vidlund et al. |
| 2004/0148020 A1 | 7/2004 | Vidlund et al. |
| 2004/0153052 A1 | 8/2004 | Mathis |
| 2004/0153146 A1 | 8/2004 | Lashinski et al. |
| 2004/0153147 A1 | 8/2004 | Mathis |
| 2004/0158321 A1 | 8/2004 | Reuter et al. |
| 2004/0162610 A1 | 8/2004 | Liska et al. |
| 2004/0167539 A1 | 8/2004 | Kuehn et al. |
| 2004/0167619 A1 | 8/2004 | Case et al. |
| 2004/0167620 A1 | 8/2004 | Ortiz et al. |
| 2004/0172046 A1 | 9/2004 | Hlavka et al. |
| 2004/0176839 A1 | 9/2004 | Huynh et al. |
| 2004/0176840 A1 | 9/2004 | Langberg et al. |
| 2004/0181238 A1 | 9/2004 | Zarbatany et al. |
| 2004/0186444 A1 | 9/2004 | Daly et al. |
| 2004/0186558 A1 | 9/2004 | Pavcnik et al. |
| 2004/0186561 A1 | 9/2004 | Mcguckin, Jr. et al. |
| 2004/0186563 A1 | 9/2004 | Lobbi |
| 2004/0186565 A1 | 9/2004 | Schreck |
| 2004/0186566 A1 | 9/2004 | Hindrichs et al. |
| 2004/0193191 A1 | 9/2004 | Starksen et al. |
| 2004/0193253 A1 | 9/2004 | Thorpe et al. |
| 2004/0193260 A1 | 9/2004 | Alferness et al. |

(56) References Cited

U.S. PATENT DOCUMENTS

| | | |
|---|---|---|
| 2004/0199155 A1 | 10/2004 | Mollenauer |
| 2004/0199183 A1 | 10/2004 | Oz et al. |
| 2004/0199191 A1 | 10/2004 | Schwartz |
| 2004/0204758 A1 | 10/2004 | Eberhardt et al. |
| 2004/0206363 A1 | 10/2004 | Mccarthy et al. |
| 2004/0210240 A1 | 10/2004 | Saint |
| 2004/0210301 A1 | 10/2004 | Obermiller |
| 2004/0210303 A1 | 10/2004 | Sedransk |
| 2004/0210304 A1 | 10/2004 | Seguin et al. |
| 2004/0210305 A1 | 10/2004 | Shu et al. |
| 2004/0210306 A1 | 10/2004 | Quijano et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0220654 A1 | 11/2004 | Mathis et al. |
| 2004/0220657 A1 | 11/2004 | Nieminen et al. |
| 2004/0225322 A1 | 11/2004 | Garrison et al. |
| 2004/0225344 A1 | 11/2004 | Hoffa et al. |
| 2004/0225348 A1 | 11/2004 | Case et al. |
| 2004/0225352 A1 | 11/2004 | Osborne et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0225356 A1 | 11/2004 | Frater |
| 2004/0230117 A1 | 11/2004 | Tosaya et al. |
| 2004/0230297 A1 | 11/2004 | Thornton |
| 2004/0236411 A1 | 11/2004 | Sarac et al. |
| 2004/0236418 A1 | 11/2004 | Stevens |
| 2004/0236419 A1 | 11/2004 | Milo |
| 2004/0243153 A1 | 12/2004 | Liddicoat et al. |
| 2004/0243219 A1 | 12/2004 | Fischer et al. |
| 2004/0243227 A1 | 12/2004 | Starksen et al. |
| 2004/0243228 A1 | 12/2004 | Kowalsky et al. |
| 2004/0243230 A1 | 12/2004 | Navia et al. |
| 2004/0254600 A1 | 12/2004 | Zarbatany et al. |
| 2004/0254636 A1 | 12/2004 | Flagle et al. |
| 2004/0260276 A1 | 12/2004 | Rudko et al. |
| 2004/0260317 A1 | 12/2004 | Bloom et al. |
| 2004/0260322 A1 | 12/2004 | Rudko et al. |
| 2004/0260389 A1* | 12/2004 | Case et al. .................. 623/1.24 |
| 2004/0260390 A1 | 12/2004 | Sarac et al. |
| 2004/0260393 A1 | 12/2004 | Rahdert et al. |
| 2004/0260394 A1 | 12/2004 | Douk et al. |
| 2004/0267357 A1 | 12/2004 | Allen et al. |
| 2005/0004583 A1 | 1/2005 | Oz et al. |
| 2005/0004667 A1 | 1/2005 | Swinford et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0021056 A1 | 1/2005 | St. Goar et al. |
| 2005/0021136 A1 | 1/2005 | Xie et al. |
| 2005/0027261 A1 | 2/2005 | Weaver et al. |
| 2005/0027348 A1 | 2/2005 | Case et al. |
| 2005/0027351 A1 | 2/2005 | Reuter et al. |
| 2005/0027353 A1 | 2/2005 | Alferness et al. |
| 2005/0033398 A1 | 2/2005 | Seguin |
| 2005/0033419 A1 | 2/2005 | Alferness et al. |
| 2005/0033446 A1 | 2/2005 | Deem et al. |
| 2005/0038506 A1 | 2/2005 | Webler et al. |
| 2005/0038507 A1 | 2/2005 | Alferness et al. |
| 2005/0043790 A1 | 2/2005 | Seguin |
| 2005/0043792 A1 | 2/2005 | Solem |
| 2005/0049679 A1 | 3/2005 | Taylor et al. |
| 2005/0049692 A1 | 3/2005 | Numamoto et al. |
| 2005/0049696 A1 | 3/2005 | Siess et al. |
| 2005/0049697 A1 | 3/2005 | Sievers |
| 2005/0054977 A1 | 3/2005 | Laird et al. |
| 2005/0055079 A1 | 3/2005 | Duran |
| 2005/0055087 A1 | 3/2005 | Starksen |
| 2005/0055088 A1 | 3/2005 | Liddicoat et al. |
| 2005/0055089 A1 | 3/2005 | Macoviak et al. |
| 2005/0060029 A1 | 3/2005 | Le et al. |
| 2005/0060030 A1 | 3/2005 | Lashinski et al. |
| 2005/0065460 A1 | 3/2005 | Laird |
| 2005/0065550 A1 | 3/2005 | Starksen et al. |
| 2005/0065594 A1 | 3/2005 | DiMatteo et al. |
| 2005/0065597 A1 | 3/2005 | Lansac |
| 2005/0070998 A1 | 3/2005 | Rourke et al. |
| 2005/0075584 A1 | 4/2005 | Cali |
| 2005/0075659 A1 | 4/2005 | Realyvasquez et al. |
| 2005/0075662 A1 | 4/2005 | Pedersen et al. |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075723 A1 | 4/2005 | Schroeder et al. |
| 2005/0075724 A1 | 4/2005 | Svanidze et al. |
| 2005/0075725 A1 | 4/2005 | Rowe |
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080483 A1 | 4/2005 | Solem et al. |
| 2005/0085900 A1 | 4/2005 | Case et al. |
| 2005/0085903 A1 | 4/2005 | Lau |
| 2005/0085904 A1 | 4/2005 | Lemmon |
| 2005/0090846 A1 | 4/2005 | Pedersen et al. |
| 2005/0096735 A1 | 5/2005 | Hojeibane et al. |
| 2005/0096738 A1 | 5/2005 | Cali et al. |
| 2005/0096739 A1 | 5/2005 | Cao |
| 2005/0096740 A1 | 5/2005 | Langberg et al. |
| 2005/0101975 A1 | 5/2005 | Nguyen et al. |
| 2005/0102026 A1 | 5/2005 | Turner et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107872 A1 | 5/2005 | Mensah et al. |
| 2005/0113910 A1 | 5/2005 | Paniagua et al. |
| 2005/0119673 A1 | 6/2005 | Gordon et al. |
| 2005/0119734 A1 | 6/2005 | Spence et al. |
| 2005/0119735 A1 | 6/2005 | Spence et al. |
| 2005/0125011 A1 | 6/2005 | Spence et al. |
| 2005/0131438 A1 | 6/2005 | Cohn |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137676 A1 | 6/2005 | Richardson et al. |
| 2005/0137681 A1 | 6/2005 | Shoemaker et al. |
| 2005/0137682 A1 | 6/2005 | Justino |
| 2005/0137685 A1 | 6/2005 | Nieminen et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0143810 A1 | 6/2005 | Dauner et al. |
| 2005/0143811 A1 | 6/2005 | Realyvasquez |
| 2005/0149014 A1 | 7/2005 | Hauck et al. |
| 2005/0149179 A1 | 7/2005 | Mathis et al. |
| 2005/0149180 A1 | 7/2005 | Mathis et al. |
| 2005/0149181 A1 | 7/2005 | Eberhardt |
| 2005/0159810 A1 | 7/2005 | Filsoufi |
| 2005/0159811 A1 | 7/2005 | Lane |
| 2005/0165477 A1 | 7/2005 | Anduiza et al. |
| 2005/0165478 A1 | 7/2005 | Song |
| 2005/0171472 A1 | 8/2005 | Lutter |
| 2005/0171601 A1 | 8/2005 | Cosgrove et al. |
| 2005/0177227 A1 | 8/2005 | Heim et al. |
| 2005/0177228 A1 | 8/2005 | Solem et al. |

(56) References Cited

U.S. PATENT DOCUMENTS

| | | |
|---|---|---|
| 2005/0182483 A1 | 8/2005 | Osborne et al. |
| 2005/0184122 A1 | 8/2005 | Hlavka et al. |
| 2005/0187614 A1 | 8/2005 | Agnew |
| 2005/0187616 A1 | 8/2005 | Realyvasquez |
| 2005/0187617 A1 | 8/2005 | Navia |
| 2005/0192606 A1 | 9/2005 | Paul, Jr. et al. |
| 2005/0192665 A1 | 9/2005 | Spenser et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216039 A1 | 9/2005 | Lederman |
| 2005/0216077 A1 | 9/2005 | Mathis et al. |
| 2005/0216078 A1 | 9/2005 | Starksen et al. |
| 2005/0222675 A1 | 10/2005 | Sauter |
| 2005/0222678 A1 | 10/2005 | Lashinski et al. |
| 2005/0228422 A1 | 10/2005 | Machold et al. |
| 2005/0228479 A1 | 10/2005 | Pavcnik et al. |
| 2005/0228486 A1 | 10/2005 | Case et al. |
| 2005/0228494 A1 | 10/2005 | Marquez |
| 2005/0228495 A1 | 10/2005 | Macoviak |
| 2005/0228496 A1 | 10/2005 | Mensah et al. |
| 2005/0234541 A1 | 10/2005 | Hunt et al. |
| 2005/0234546 A1 | 10/2005 | Nugent et al. |
| 2005/0240200 A1 | 10/2005 | Bergheim |
| 2005/0240202 A1 | 10/2005 | Shennib et al. |
| 2005/0240255 A1 | 10/2005 | Schaeffer |
| 2005/0240259 A1 | 10/2005 | Sisken et al. |
| 2005/0240262 A1 | 10/2005 | White |
| 2005/0244460 A1 | 11/2005 | Alferiev et al. |
| 2005/0246013 A1 | 11/2005 | Gabbay |
| 2005/0251251 A1 | 11/2005 | Cribier |
| 2005/0256566 A1 | 11/2005 | Gabbay |
| 2005/0261704 A1 | 11/2005 | Mathis |
| 2005/0261759 A1 | 11/2005 | Lambrecht et al. |
| 2005/0267493 A1 | 12/2005 | Schreck et al. |
| 2005/0267560 A1 | 12/2005 | Bates |
| 2005/0267565 A1 | 12/2005 | Dave et al. |
| 2005/0267571 A1 | 12/2005 | Spence et al. |
| 2005/0267573 A9 | 12/2005 | Macoviak et al. |
| 2005/0267574 A1 | 12/2005 | Cohn et al. |
| 2005/0272969 A1 | 12/2005 | Alferness et al. |
| 2005/0273160 A1 | 12/2005 | Lashinski et al. |
| 2005/0278015 A1 | 12/2005 | Dave et al. |
| 2005/0283178 A1 | 12/2005 | Flagle et al. |
| 2005/0288779 A1 | 12/2005 | Shaoulian et al. |
| 2006/0000715 A1 | 1/2006 | Whitcher et al. |
| 2006/0004439 A1 | 1/2006 | Spenser et al. |
| 2006/0004442 A1 | 1/2006 | Spenser et al. |
| 2006/0009804 A1 | 1/2006 | Pederson |
| 2006/0009841 A1 | 1/2006 | Mcguckin, Jr. et al. |
| 2006/0009842 A1 | 1/2006 | Huynh et al. |
| 2006/0013805 A1 | 1/2006 | Hebbel et al. |
| 2006/0013855 A1 | 1/2006 | Carpenter et al. |
| 2006/0015136 A1 | 1/2006 | Besselink |
| 2006/0015178 A1 | 1/2006 | Moaddeb et al. |
| 2006/0015179 A1 | 1/2006 | Bulman-Fleming et al. |
| 2006/0020275 A1 | 1/2006 | Goldfarb |
| 2006/0020327 A1 | 1/2006 | Lashinski et al. |
| 2006/0020332 A1 | 1/2006 | Lashinski et al. |
| 2006/0020334 A1 | 1/2006 | Lashinski et al. |
| 2006/0020335 A1 | 1/2006 | Kowalsky et al. |
| 2006/0020336 A1 | 1/2006 | Liddicoat |
| 2006/0025750 A1 | 2/2006 | Startksen et al. |
| 2006/0025784 A1 | 2/2006 | Startksen et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0025856 A1 | 2/2006 | Ryan et al. |
| 2006/0025857 A1 | 2/2006 | Bergheim et al. |
| 2006/0030747 A1 | 2/2006 | Kantrowitz et al. |
| 2006/0030866 A1 | 2/2006 | Schreck |
| 2006/0030882 A1 | 2/2006 | Adams et al. |
| 2006/0030885 A1 | 2/2006 | Hyde |
| 2006/0036317 A1 | 2/2006 | Vidlund et al. |
| 2006/0041305 A1 | 2/2006 | Lauterjung |
| 2006/0041306 A1 | 2/2006 | Vidlund et al. |
| 2006/0047297 A1 | 3/2006 | Case |
| 2006/0047338 A1 | 3/2006 | Jenson |
| 2006/0047343 A1 | 3/2006 | Oviatt et al. |
| 2006/0052804 A1 | 3/2006 | Mialhe |
| 2006/0052867 A1 | 3/2006 | Revuelta et al. |
| 2006/0058817 A1 | 3/2006 | Starksen et al. |
| 2006/0058865 A1 | 3/2006 | Case et al. |
| 2006/0058871 A1 | 3/2006 | Zakay et al. |
| 2006/0058889 A1 | 3/2006 | Case et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0064174 A1 | 3/2006 | Zadno |
| 2006/0069400 A1 | 3/2006 | Burnett et al. |
| 2006/0069429 A1 | 3/2006 | Spence et al. |
| 2006/0069430 A9 | 3/2006 | Rahdert et al. |
| 2006/0074483 A1 | 4/2006 | Schrayer |
| 2006/0074484 A1 | 4/2006 | Huber |
| 2006/0074485 A1 | 4/2006 | Realyvasquez |
| 2006/0085060 A1 | 4/2006 | Campbell |
| 2006/0089708 A1 | 4/2006 | Osse et al. |
| 2006/0095115 A1 | 5/2006 | Bladilah et al. |
| 2006/0095125 A1 | 5/2006 | Chinn et al. |
| 2006/0099326 A1 | 5/2006 | Keogh et al. |
| 2006/0100697 A1 | 5/2006 | Casanova |
| 2006/0100699 A1 | 5/2006 | Vidlund et al. |
| 2006/0106278 A1 | 5/2006 | Machold et al. |
| 2006/0106279 A1 | 5/2006 | Machold et al. |
| 2006/0106456 A9 | 5/2006 | Machold et al. |
| 2006/0111660 A1 | 5/2006 | Wolf et al. |
| 2006/0111773 A1 | 5/2006 | Rittgers et al. |
| 2006/0111774 A1 | 5/2006 | Samkov et al. |
| 2006/0116572 A1 | 6/2006 | Case |
| 2006/0116756 A1 | 6/2006 | Solem et al. |
| 2006/0122686 A1 | 6/2006 | Gilad et al. |
| 2006/0122692 A1 | 6/2006 | Gilad et al. |
| 2006/0122693 A1 | 6/2006 | Biadillah et al. |
| 2006/0127443 A1 | 6/2006 | Helmus |
| 2006/0129235 A1 | 6/2006 | Seguin et al. |
| 2006/0129236 A1 | 6/2006 | Mccarthy |
| 2006/0135476 A1 | 6/2006 | Kutryk et al. |
| 2006/0135964 A1 | 6/2006 | Vesely |
| 2006/0135967 A1 | 6/2006 | Realyvasquez |
| 2006/0136044 A1 | 6/2006 | Osborne |
| 2006/0136045 A1 | 6/2006 | Flagle et al. |
| 2006/0136052 A1 | 6/2006 | Vesely |
| 2006/0136054 A1 | 6/2006 | Berg et al. |
| 2006/0142846 A1 | 6/2006 | Pavcnik et al. |
| 2006/0142847 A1 | 6/2006 | Shaknovich |
| 2006/0142848 A1 | 6/2006 | Gabbay |
| 2006/0142854 A1 | 6/2006 | Alferness et al. |
| 2006/0149358 A1 | 7/2006 | Zilla et al. |
| 2006/0149360 A1 | 7/2006 | Schwammenthal et al. |
| 2006/0149367 A1 | 7/2006 | Sieracki |
| 2006/0149368 A1 | 7/2006 | Spence |
| 2006/0161133 A1 | 7/2006 | Laird et al. |
| 2006/0161248 A1 | 7/2006 | Case et al. |
| 2006/0161249 A1 | 7/2006 | Realyvasquez et al. |
| 2006/0161250 A1 | 7/2006 | Shaw |
| 2006/0167468 A1 | 7/2006 | Gabbay |
| 2006/0167541 A1 | 7/2006 | Lattouf |
| 2006/0167542 A1 | 7/2006 | Quintessenza |
| 2006/0167543 A1 | 7/2006 | Bailey |

FOREIGN PATENT DOCUMENTS

| | | |
|---|---|---|
| FR | 2728457 | 6/1996 |
| WO | 8800459 | 1/1988 |
| WO | 9015582 | 12/1990 |
| WO | 9501669 | 1/1995 |
| WO | 9619159 | 6/1996 |

(56) References Cited

FOREIGN PATENT DOCUMENTS

| | | |
|---|---|---|
| WO | 9803656 | 1/1998 |
| WO | 9846115 | 10/1998 |
| WO | 9904724 | 2/1999 |
| WO | 0067679 | 11/2000 |
| WO | 0115650 | 3/2001 |
| WO | 0117462 | 3/2001 |
| WO | 0166043 | 9/2001 |
| WO | 03047468 | 6/2003 |
| WO | 03084443 | 10/2003 |
| WO | 2004019825 | 3/2004 |
| WO | 2004021893 | 3/2004 |
| WO | 2004023980 | 3/2004 |
| WO | 2004030568 | 4/2004 |
| WO | 2004030569 | 4/2004 |
| WO | 2004030570 | 4/2004 |
| WO | 2004032724 | 4/2004 |
| WO | 2004032796 | 4/2004 |
| WO | 2004037128 | 5/2004 |
| WO | 2004037317 | 5/2004 |
| WO | 2004039432 | 5/2004 |
| WO | 2004043265 | 5/2004 |
| WO | 2004043273 | 5/2004 |
| WO | 2004043293 | 5/2004 |
| WO | 2004045370 | 6/2004 |
| WO | 2004045378 | 6/2004 |
| WO | 2004045463 | 6/2004 |
| WO | 2004047677 | 6/2004 |
| WO | 2004060217 | 7/2004 |
| WO | 2004060470 | 7/2004 |
| WO | 2004062725 | 7/2004 |
| WO | 2004066803 | 8/2004 |
| WO | 2004066826 | 8/2004 |
| WO | 2004069287 | 8/2004 |
| WO | 2004075789 | 9/2004 |
| WO | 2004080352 | 9/2004 |
| WO | 2004082523 | 9/2004 |
| WO | 2004082527 | 9/2004 |
| WO | 2004082528 | 9/2004 |
| WO | 2004082536 | 9/2004 |
| WO | 2004082537 | 9/2004 |
| WO | 2004082538 | 9/2004 |
| WO | 2004082757 | 9/2004 |
| WO | 2004084746 | 10/2004 |
| WO | 2004084770 | 10/2004 |
| WO | 2004089246 | 10/2004 |
| WO | 2004089250 | 10/2004 |
| WO | 2004089253 | 10/2004 |
| WO | 2004091449 | 10/2004 |
| WO | 2004091454 | 10/2004 |
| WO | 2004093638 | 11/2004 |
| WO | 2004093726 | 11/2004 |
| WO | 2004093728 | 11/2004 |
| WO | 2004093730 | 11/2004 |
| WO | 2004093745 | 11/2004 |
| WO | 2004093935 | 11/2004 |
| WO | 2004096100 | 11/2004 |
| WO | 2004103222 | 12/2004 |
| WO | 2004103223 | 12/2004 |
| WO | 2004105584 | 12/2004 |
| WO | 2004105651 | 12/2004 |
| WO | 2004112582 | 12/2004 |
| WO | 2004112585 | 12/2004 |
| WO | 2004112643 | 12/2004 |
| WO | 2004112652 | 12/2004 |
| WO | 2004112657 | 12/2004 |
| WO | 2004112658 | 12/2004 |
| WO | 2005000152 | 1/2005 |
| WO | 2005002424 | 1/2005 |
| WO | 2005002466 | 1/2005 |
| WO | 2005004753 | 1/2005 |
| WO | 2005007017 | 1/2005 |
| WO | 2005007018 | 1/2005 |
| WO | 2005007036 | 1/2005 |
| WO | 2005007037 | 1/2005 |
| WO | 2005009285 | 2/2005 |
| WO | 2005009286 | 2/2005 |
| WO | 2005009505 | 2/2005 |
| WO | 2005009506 | 2/2005 |
| WO | 2005011473 | 2/2005 |
| WO | 2005011534 | 2/2005 |
| WO | 2005011535 | 2/2005 |
| WO | 2005013860 | 2/2005 |
| WO | 2005018507 | 3/2005 |
| WO | 2005021063 | 3/2005 |
| WO | 2005023155 | 3/2005 |
| WO | 2005025644 | 3/2005 |
| WO | 2005027790 | 3/2005 |
| WO | 2005027797 | 3/2005 |
| WO | 2005034812 | 4/2005 |
| WO | 2005039428 | 5/2005 |
| WO | 2005039452 | 5/2005 |
| WO | 2005046488 | 5/2005 |
| WO | 2005046528 | 5/2005 |
| WO | 2005046529 | 5/2005 |
| WO | 2005046530 | 5/2005 |
| WO | 2005046531 | 5/2005 |
| WO | 2005048883 | 6/2005 |
| WO | 2005049103 | 6/2005 |
| WO | 2005051226 | 6/2005 |
| WO | 2005055811 | 6/2005 |
| WO | 2005055883 | 6/2005 |
| WO | 2005058206 | 6/2005 |
| WO | 2005065585 | 7/2005 |
| WO | 2005065593 | 7/2005 |
| WO | 2005065594 | 7/2005 |
| WO | 2005070342 | 8/2005 |
| WO | 2005070343 | 8/2005 |
| WO | 2005072654 | 8/2005 |
| WO | 2005072655 | 8/2005 |
| WO | 2005079706 | 9/2005 |
| WO | 2005082288 | 9/2005 |
| WO | 2005082289 | 9/2005 |
| WO | 2005084595 | 9/2005 |
| WO | 2005087139 | 9/2005 |
| WO | 2005087140 | 9/2005 |
| WO | 2006000763 | 1/2006 |
| WO | 2006000776 | 1/2006 |
| WO | 2006002492 | 1/2006 |
| WO | 2006004679 | 1/2006 |
| WO | 2006005015 | 1/2006 |
| WO | 2006009690 | 1/2006 |
| WO | 2006011127 | 2/2006 |
| WO | 2006012011 | 2/2006 |
| WO | 2006012013 | 2/2006 |
| WO | 2006012038 | 2/2006 |
| WO | 2006012068 | 2/2006 |
| WO | 2006012322 | 2/2006 |
| WO | 2006019498 | 2/2006 |
| WO | 2006026371 | 3/2006 |
| WO | 2006026377 | 3/2006 |
| WO | 2006026912 | 3/2006 |
| WO | 2006027499 | 3/2006 |
| WO | 2006028821 | 3/2006 |
| WO | 2006029062 | 3/2006 |
| WO | 2006031436 | 3/2006 |
| WO | 2006031469 | 3/2006 |
| WO | 2006032051 | 3/2006 |
| WO | 2006034245 | 3/2006 |
| WO | 2006035415 | 4/2006 |
| WO | 2006041505 | 4/2006 |
| WO | 2006044679 | 4/2006 |
| WO | 2006048664 | 5/2006 |
| WO | 2006050459 | 5/2006 |
| WO | 2006050460 | 5/2006 |
| WO | 2006054107 | 5/2006 |
| WO | 2006054930 | 5/2006 |
| WO | 2006055982 | 5/2006 |
| WO | 2006060546 | 6/2006 |
| WO | 2006063108 | 6/2006 |
| WO | 2006063181 | 6/2006 |
| WO | 2006063199 | 6/2006 |
| WO | 2006064490 | 6/2006 |
| WO | 2006065212 | 6/2006 |
| WO | 2006065930 | 6/2006 |

(56) References Cited

FOREIGN PATENT DOCUMENTS

| | | |
|---|---|---|
| WO | 2006066148 | 6/2006 |
| WO | 2006066150 | 6/2006 |
| WO | 2006069094 | 6/2006 |
| WO | 2006070372 | 7/2006 |
| WO | 2006073628 | 7/2006 |
| WO | 2006076890 | 7/2006 |

* cited by examiner

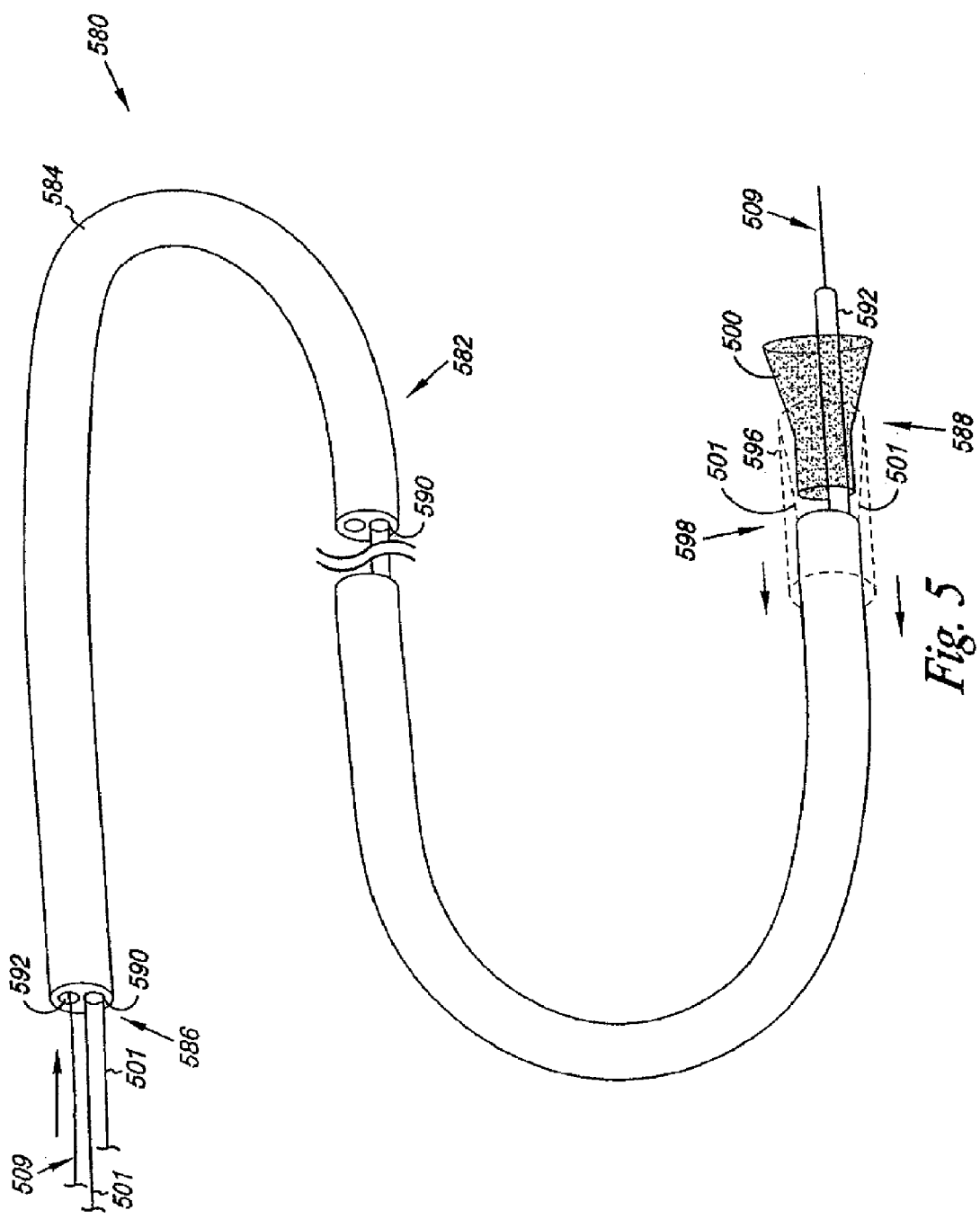

US 8,672,997 B2

VALVE WITH SINUS

CROSS-REFERENCE TO RELATED APPLICATIONS

This application is a Continuation of U.S. application Ser. No. 11/652,299, filed Jan. 11, 2007 now abandoned, which is a Continuation-in Part of U.S. application Ser. No. 11/232,403, filed Sep. 21, 2005 now U.S. Pat. No. 7,569,071, the specification of each of which is incorporated by reference herein.

FIELD OF THE DISCLOSURE

The present disclosure relates to vascular medical devices and methods; and more particularly to valves and methods for forming the valve frame.

BACKGROUND OF THE DISCLOSURE

Venous blood flow returns de-oxygenated blood from the distal extremities to the heart via two mechanisms. The first is the perfusion pressure resulting from the arterial blood flow through tissue to the venous circulation system. Where arterial pressure prior to perfusion may be 60 to 200 mm Hg, the resulting venous pressure is typically 10 to 40 mm Hg. The second mechanism is the calf muscle, which, when contracted, compresses the veins (tibial and peroneal) overlying the bone and, through a system of valves, directs blood flow toward the heart. This is the organized flow of blood through a normal, healthy person.

Venous valves, especially those in the upper leg, perform an important function. When a person rises from a seated to a standing position, arterial blood pressure increases instantaneously to insure adequate perfusion to the brain and other critical organs. In the legs and arms, the transit time of this increased arterial pressure is delayed, resulting in a temporary drop in venous pressure. Venous pressure drops as blood flow responds to body position change and gravity, thereby reducing the volume of blood available to the heart and possibly reducing the flow of oxygenated blood to the brain. In such a case, a person could become light headed, dizzy, or experience syncope. It is the function of valves in the iliac, femoral and, to a lesser degree, more distal vein valves to detect these drops in pressure and resulting change of direction of blood flow and to close to prevent blood from pooling in the legs to maintain blood volume in the heart and head. The valves reopen and the system returns to normal forward flow when the reflected arterial pressure again appears in the venous circulation. Compromised valves, however, would allow reverse blood flow and pooling in the lower legs resulting in swelling and ulcers of the leg. The absence of functioning venous valves can lead to chronic venous insufficiency.

Techniques for both repairing and replacing the valves exist, but are tedious and require invasive surgical procedures. Direct and indirect valvuoplasty procedures are used to repair damaged valves. Transposition and transplantation are used to replace an incompetent valve. Transposition involves moving a vein with an incompetent valve to a site with a competent valve. Transplantation replaces an incompetent valve with a harvested valve from another venous site.

Prosthetic valves can be transplanted into the venous system, but current devices are not successful enough to see widespread usage. One reason for this is the very high percentage of prosthetic valves reported with leaflet functional failures due to excessive protein deposit, cell growth and thickening, and thrombosis. These failures have been blamed primarily on improper sizing and tilted deployment of the prosthetic valve. In addition, a great number of the valve leaflets come into close proximity to or in contact with the adjacent vessel wall, conduit, or supporting frame of the valve. Such contact or proximity can cause regions of blood stasis or near stasis, and can result in increased thrombus formation. In addition, contact can result in disruption of endothelial or other tissue at the contact point, further increasing the likelihood of thrombosis or increased tissue deposits or healing response. Further, such contact or proximity can result in valve leaflet(s) being stuck to the vessel wall, or otherwise unable to move properly, thereby rendering the valve less functional or completely non-functional.

BRIEF DESCRIPTION OF THE DRAWINGS

FIG. 5 illustrates an embodiment of a system that includes a valve according to the present disclosure.

DETAILED DESCRIPTION

Figure 1A:
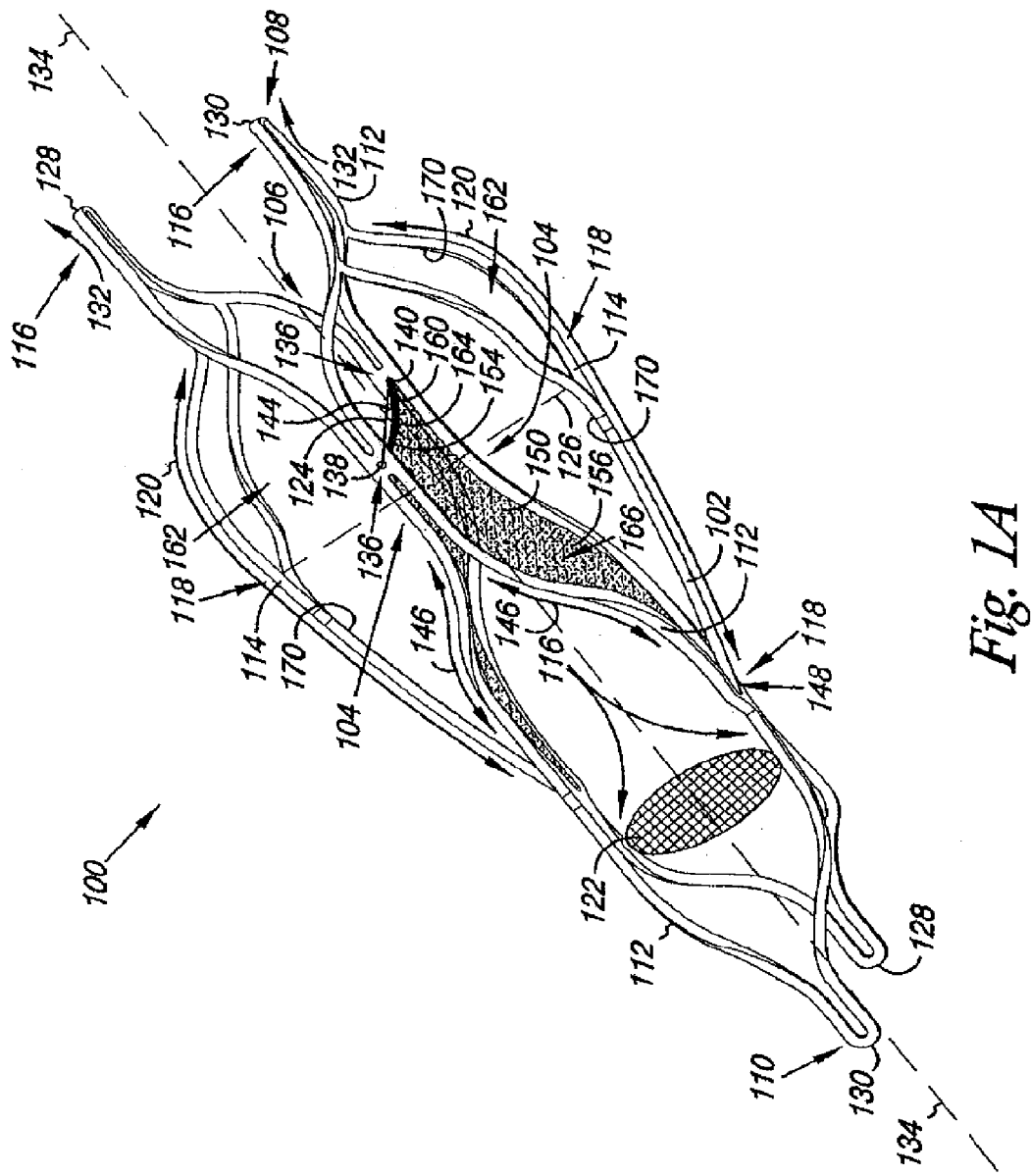
FIGS. 1A and 1B illustrate an embodiment of a valve according to the present disclosure.

Embodiments of the present disclosure are directed to vascular medical devices and methods for valve replacement and/or augmentation. Particularly, the present disclosure provides venous valves and methods for forming the venous valve. Various embodiments of the present disclosure can be used to replace and/or augment an incompetent valve in a body lumen. As used herein, "body lumen" can include, but is not limited to, veins, arteries, lymph vessels, ureter, cerebrospinal fluid track, or other body cavity, vessel, or duct.

Embodiments of the valve include a valve frame and valve leaflets that can be implanted through minimally-invasive techniques into the body lumen. In one example, embodiments of the apparatus and method for valve replacement or augmentation may help to maintain antegrade blood flow, while decreasing retrograde blood flow in a venous system of individuals having venous insufficiency, such as venous insufficiency in the legs. Use of valve embodiments can also be possible in other portions of the vasculature.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of valve. In addition, discussion of features and/or attributes for an element with respect to one Figure can also apply to the element shown in one or more additional Figures. Embodiments illustrated in the figures are not necessarily to scale.

Figure 1B:
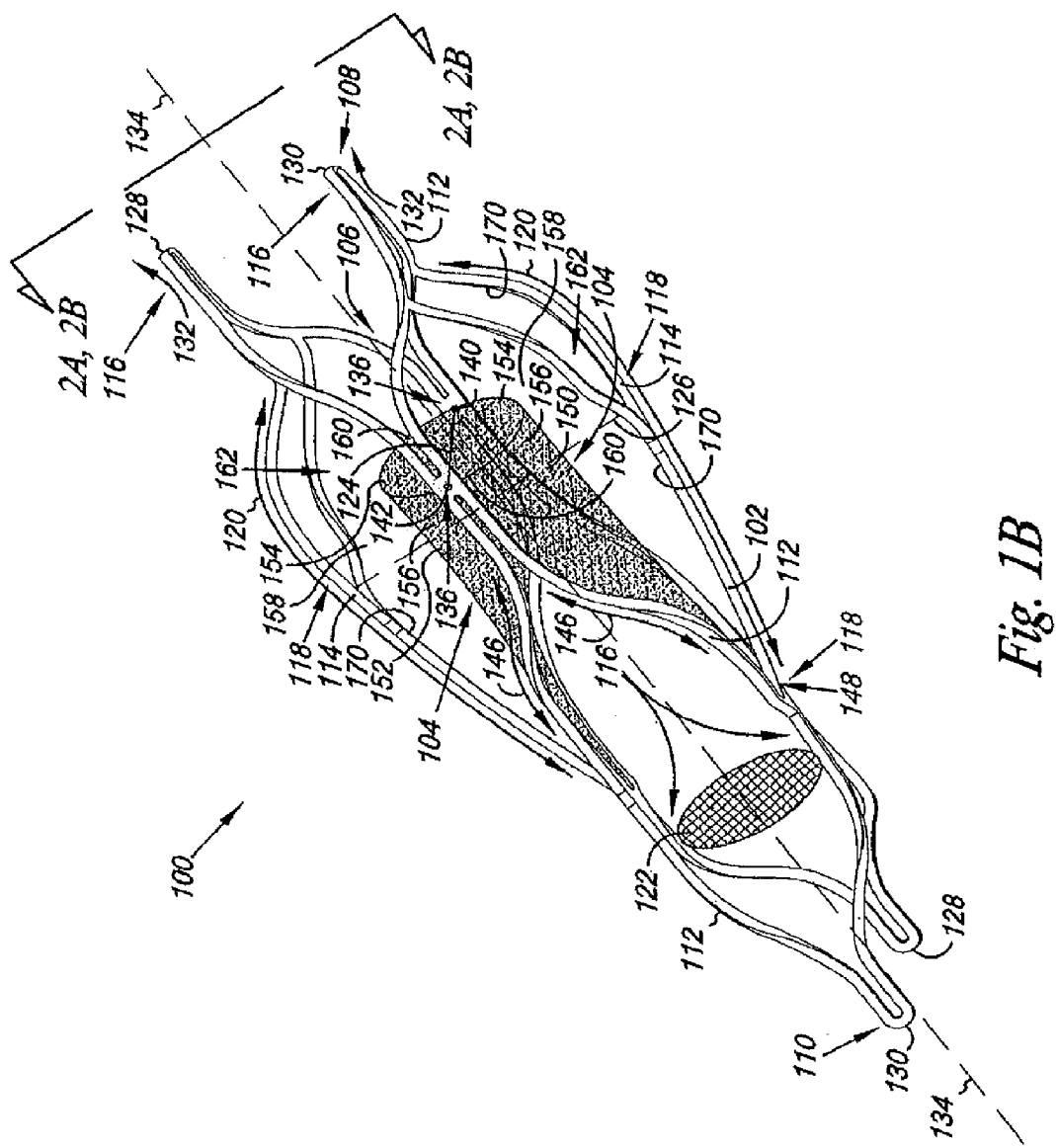

FIGS. 1A and 1B provide illustrations of various embodiments of a venous valve 100 of the present disclosure. The venous valve 100 can be implanted within the fluid passageway of a body lumen, such as for replacement and/or augmentation of a valve structure within the body lumen (e.g., a venous valve). In one embodiment, the venous valve 100 of the present disclosure may be beneficial to regulate the flow of a bodily fluid through the body lumen in a single direction.

FIGS. 1A and 1B illustrate one embodiment of the venous valve 100. Valve 100 includes a valve frame 102 and valve leaflets 104. In one embodiment, the valve frame 102 and the valve leaflets 104 of the valve 100 can resiliently radially collapse and expand, as will be described herein. Among other things, the valve frame 102 and the valve leaflets 104 define a lumen 106 of the valve 100. The lumen 106 allows for, amongst other things, fluid (e.g., blood) to move through the valve 100.

The valve frame 102 includes a first end 108 and a second end 110 opposite the first end 108. The first end 108 and the second end 110 define a length of the valve frame 102 and of the valve 100. In one embodiment, the length of valve 100 can have a number of values. As will be appreciated, the length of valve 100 can be determined based upon the location into which the valve 100 is to be implanted. In other words, the length of the valve 100 can be patient specific. Examples of values for the length include, but are not limited to, 20 millimeters to 80 millimeters. Other values are also possible.

The valve frame 102 can be formed in a wide variety of configurations. For example, the valve frame 102 can include a first structural member 112 and a second structural member 114 that together form a unitary structure with an open frame configuration. In one embodiment, the first structural member 112 defines an elongate base portion 116 that extends between the first end 108 and the second end 110 of the valve frame 102. As illustrated, the first structural member 112 defines openings through the valve frame 102 to provide at least a portion of the open frame configuration.

In addition, the first structural member 112 also defines a first perimeter value for the elongate base portion 116. In one embodiment, the first perimeter value can be essentially constant for the length of the valve frame 102. In other words, the outer limit of the area defined by the elongate base portion 116 remains essentially constant along the length of the valve frame 102. For example, an outer surface 118 of the first structural member 112 can define a circular cross-sectional area for the elongate base portion 116. As will be appreciated, other cross-sectional shapes are also possible, including but not limited to oval or elliptical.

In an alternative embodiment, the perimeter value changes along the length of the valve frame 102. For example, the outer surface 118 of the first structural member 112 can change from a first cross-sectional area having a first value for the elongate base portion 116 adjacent the first end 108 and the second end 110 to a second cross-sectional area having a second value larger than the first value. In one embodiment, the second cross-sectional area of the outer surface 118 of the first structural member 112 can, in conjunction with the second structural member 114 provide for a circular or round cross-sectional shape. Other cross-sectional shapes are also possible.

In an additional embodiment, the second structural member 114 helps to define a bulbous portion 120 of the valve frame 102. As illustrated, the second structural member 114 extends radially and longitudinally from the outer surface 118 of an area 122 defined by the first structural member 112 to form the bulbous portion 120. In one embodiment, the second structural member 114 helps to define a second perimeter value for the bulbous portion 120, where second perimeter value can be is greater than the first perimeter value.

As illustrated, the outer surface 118 of the first and second structural members 112, 114 can provide a perimeter of the bulbous portion 120 and the elongate base portion 116 having a predefined shape. For example, the first structural member 112 can define a first axis 124 of an elliptical shape and the second structural member 114 can define a second axis 126 of the elliptical shape. In one embodiment, the length of the second axis 126 can be at least twenty percent (20%) greater than the length of the first axis 124. In an additional embodiment, the length of the second axis 126 can be twenty percent (20%) to fifty percent (50%) greater than the length of the first axis 124. In a further embodiment, the length of the second axis 126 can be forty percent (40%) to forty-two percent (42%) greater than the length of the first axis 124.

In an additional embodiment, the length of the second axis 126 can be one (1) to four (4) millimeters greater than the length of the first axis 124. As will be more fully discussed herein, this allows for a gap 158 of one-half (0.5) to two (2) millimeters to be maintained between a free edge 160 of the valve leaflets 104 in their open configuration and the valve frame 102. In one embodiment, the length of the gap 158 between each leaflet 104 and the valve frame 102 can be, but is not necessarily, equal. The gap is shown in greater detail in FIGS. 9A-C.

In an additional example, the perimeter of the bulbous portion 120 and the elongate base portion 116 can have a round shape. For example, the first axis 124 of the first structure member 112 and the second axis 126 of the second structural member 114 can be essentially of equal length along the bulbous portion 120.

Figure 2A:
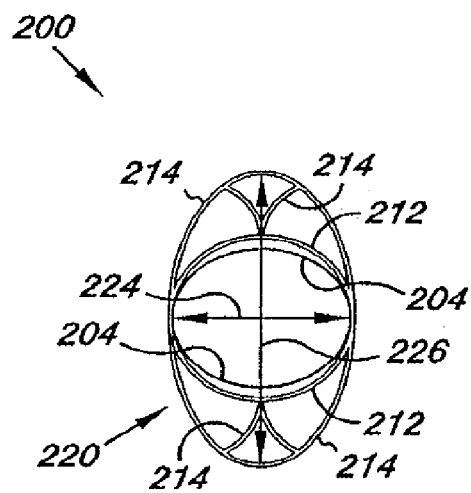
FIGS. 2A and 2B illustrate an end view of embodiments of a valve according to the present disclosure.
Figure 2B:
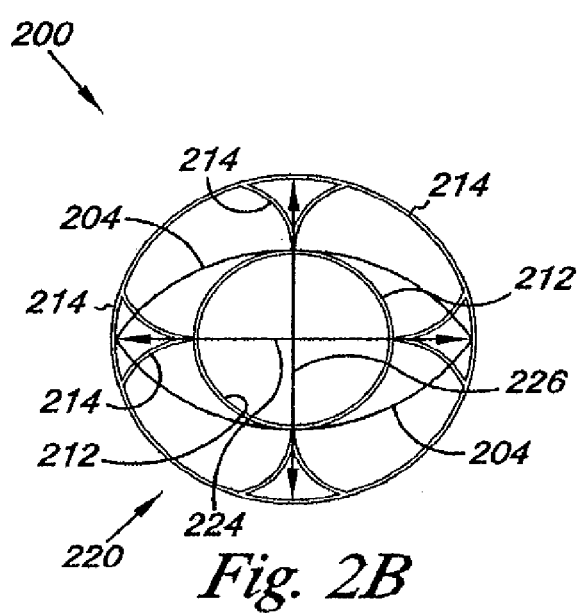

FIGS. 2A and 2B illustrate embodiments of the valve 200 according to the present disclosure. The embodiments illustrated in FIGS. 2A and 2B are end views of the valve illustrated in FIG. 1A taken along lines 2A-2A/2B-2B. As discussed herein, FIG. 2A illustrates the valve 200 where the first structural member 212 defining the first axis 224 and the second structural member 214 defining the second axis 226 provide an elliptical shape for the bulbous portion 220 of the valve frame 202. FIG. 2B illustrates the valve 200 where the first structural member 212 defining the first axis 224 and the second structural member 214 defining the second axis 226 provide a round shape for the bulbous portion 220 of the valve frame 202.

In addition, the first structural member 112 at each of the first end 108 and the second end 110 can include a first curve 128 and a second curve 130 opposite the first curve 128. In one embodiment, the first structural member 112 forming the first and second curve 128, 130 can move radially as the valve 100 radially collapses and expands. In the various embodiments described herein, the first and second curve 128, 130 can provide a spring force (e.g., elastic potential energy) to counter radial compression of the frame valve 102 towards its uncompressed state. As will be appreciated, the first and second curve 128, 130 can have a number of configurations, including turns defining angles and/or arcs (e.g., having a radius of curvature). Additional spring force can be imparted to the frame 102 from the compression of other portions of the valve frame 102 as well.

In one embodiment, the first and second curve 128, 130 at each of the ends 108, 110 can lay opposite each other on a respective plane that is parallel to the other plane. In addition, the first and second curve 128, 130 of the first end 108 can be positioned radially orthogonal to the first and second curve 128, 130 of the second end 110 of the base portion 116. As will be appreciated, the first and second curve 128, 130 at each of the ends 108, 110, however, need not either lay on planes that are parallel relative each other and/or be positioned radially orthogonal to each other.

The compressible nature of the valve 100 can accommodate changes in body lumen size (e.g., diameter of the body lumen) by flexing to expand and/or contract to change the diameter of the valve frame 102. In one embodiment, the first and second curve 128, 130 in the first structural member 112 can act as springs to allow the valve 100 to resiliently radially collapse and expand. The frame 102 can also provide sufficient contact and expansion force with the surface of a body lumen wall to encourage fixation of the valve 100 and to prevent retrograde flow within the body lumen around the edges of the frame 102 and the surface of a lumen when combined with a closed state of the valve leaflets attached thereto. Anchoring elements (e.g., barbs) can also be included with valve 100.

As will be appreciated, the first and second curve 128, 130 in the first structural member 112 can also include, but are not limited to, other shapes that allow for repeatable travel between the collapsed state and the expanded state. For example, the elastic regions can include integrated springs having a circular or an elliptical loop configuration. The embodiments are not, however, limited to these configurations as other shapes are also possible.

The first structural member 112 forming the first and second curve 128, 130 can also include a radial flare 132 that curves away from a center longitudinal axis 134. As illustrated, the radial flare 132 provides for an increase in the peripheral frame dimension at the first end 108 and/or the second end 110 of the valve frame 102. In one embodiment, the first structural member 112 can be pre- and/or post-treated to impart the radial flare 132. For example, the first structural member 112 forming the first and second curve 128, 130 of the valve frame 102 could be bent to impart the radial flare 132. The frame 102 could then be heat treated so as to fix the radial flare 132 into the first structural member 112. Other material treatments (e.g., plastic deformation, forging, elastic deformation with heat setting) are also possible to impart the radial flare as described herein, many of which are material specific.

The first structural member 112 and/or the second structural member 114 of the valve frame 102 can have similar and/or different cross-sectional geometries and/or cross-sectional dimensions along their length. The similarity and/or the differences in the cross-sectional geometries and/or cross-sectional dimensions can be based on one or more desired functions to be elicited from each portion of the frame 102. For example, the first structural member 112 and/or the second structural member 114 can have a similar cross-sectional geometry along its length. Examples of cross-sectional geometries include, but are not limited to, round (e.g., circular, oval, and/or elliptical), rectangular geometries having perpendicular sides, one or more convex sides, or one or more concave sides; semi-circular; triangular; tubular; 1-shaped; T-shaped; and trapezoidal.

Alternatively, the cross-sectional dimensions of one or more geometries of the first structural member 112 and/or the second structural member 114 can change from one portion of the frame 102 to another portion of the frame 102. For example, portions of the first structural member 112 and/or the second structural member 114 can taper (i.e., transition) from a first geometric dimension to a second geometric dimension different than the first geometric dimension. These embodiments, however, are not limited to the present examples as other cross-sectional geometries and dimension are also possible. As such, the present disclosure should not be limited to the frames provided in the illustration herein.

The valve frame 102 further includes a valve leaflet connection location 136 along the first structural member 112 of the valve frame 102. In one embodiment, the valve leaflet connection location 136 includes portions of the first structural member 112 that can define the area 122, as well as surfaces of the first structural member 112 that define openings through the frame 102. For example, the first structural member 112 can include surfaces that define a first opening 138 and a second opening 140 for the valve leaflet connection location 136. In one embodiment, the first and second openings 138, 140 are adjacent a region of the bulbous portion 120 of the valve frame 102. The first and second openings 138, 140 are also illustrated as being positioned opposite each other along a common axis 144. In the present illustration, the common axis 144 is along the first axis 124 of the shape (e.g., elliptical, round) formed by the first and second structural member 112, 114.

In an additional embodiment, the valve leaflet connection location 136 further includes a predefined portion 146 along the first structural member 112 to which the valve leaflets 104 can be attached. As illustrated, the predefined portion 146 includes a portion of the first structural member 112 that extends between the first and second openings 138, 140 in the region of the bulbous portion 120. In one embodiment, the valve leaflets 104 can be coupled to the valve frame 102 through the first and second openings 138, 140 and the predefined portion 146 of the first structural member 112.

In addition to allowing the valve leaflets 104 to be coupled to the valve frame 102, the valve leaflet connection location 140 can also include predetermined dimensional relationships between portions of the valve leaflet connection location 136. For example, predetermined dimensional relationships can exist between the relative positions of the first and second openings 138, 140 and the predefined portion 146 of the first structural member 112. These dimensional relationships can help to better position the valve leaflets 104 in relation to the bulbous portion 120 of the valve frame 102.

For example, as illustrated the predefined portion 146 of the first structural member 112 extends away from the first and second opening 138, 140 to define a distal point 148 from the first and second openings 138, 140. In one embodiment, the distance between the first and second openings 138, 140 and a plane that is both orthogonal to the center longitudinal axis 134 and in contact with the distal point 148 is a predetermined length having a value of eighty-five percent (85%) of distance of the second axis 126.

In one embodiment, the valve leaflets 104 include a first valve leaflet 150 and a second valve leaflet 152. As illustrated, the first and second valve leaflets 150, 152 are connected to the valve leaflet connection location 136. The first and second valve leaflet 150, 152 have surfaces that define a commissure 154 that reversibly opens and closes for unidirectional flow of a liquid through the valve 100. As used herein, the commissure 154 includes portions of the valve leaflet 104 surfaces that reversibly form a connection to allow fluid to flow through the valve 100 in essentially one direction. For example, the surfaces of the first and second valve leaflets 150, 152 can move between a closed configuration in which fluid flow through the lumen 106 can be restricted and an open configuration in which fluid flow through the lumen 106 can be permitted.

In addition, the first and second openings 138, 140 can be radially symmetric around the longitudinal central axis 134 of the valve frame 102. As illustrated, the first and second openings 138, 140 can be positioned approximately one hundred eighty (180) degrees relative each other around the longitudinal central axis 134 of the frame 102. As will be appreciated, the first and second openings 138, 140 need not necessarily display an equally spaced symmetrical relationship as described above in order to practice the embodiments of the present disclosure. For example, the radial relationship can have the first and second openings 138, 140 positioned at values greater than one hundred eighty (180) degrees and less than one hundred eighty (180) degrees relative each other around the longitudinal central axis 134 of the frame 102.

In the present example, the first and second valve leaflet 150, 152 can be coupled, as described more fully herein, to at least the valve leaflet connection location 136 and the predefined portion 146 of the valve frame 102. As illustrated, the valve leaflets 104 include a region 156 of the valve leaflets 104 that can move relative the valve frame 102. The region 156 of the valve leaflets 104 can be unbound (i.e., unsupported) by the frame 102 and extends between the first and second openings 138, 140. This configuration permits the first and second valve leaflet 150, 152 to move (e.g., pivot) relative the first and second openings 138, 140 to allow the commissure 154 to reversibly open and close for unidirectional flow of the liquid through the valve 100.

In an additional embodiment, the valve leaflets 104 in their open configuration have a circumference that is less than the circumference of the valve frame 102. For example, as illustrated, the valve leaflets 104 in their open configuration include a gap 158 between a free edge 160 of the first and second valve leaflets 150, 152 and the bulbous portion 120 of the valve frame 102. As discussed herein, the length of the second axis 126 can be one (1) to four (4) millimeters greater than the length of the first axis 124. In one embodiment, this allows for the gap 158 between the free edge 160 of each valve leaflet 104 in their open position to be one-half (0.5) to two (2) millimeters from the bulbous portion 120 of the valve frame 102. In one embodiment, the length of the gap 158 between each leaflet 104 and the valve frame 102 can be, but is not necessarily, equal. The gap is shown in greater detail in FIGS. 9A-C.

In one embodiment, the first and second valve leaflets 150, 152 and the bulbous portion 120 of the valve frame 102 provide surfaces that define a sinus pocket 162. As illustrated, the sinus pocket 162 provides a dilated channel or receptacle as compared to the elongate base portion 116 of the valve 100. In one embodiment, the presence of the sinus pocket 162 better ensures that the valve leaflets 104 do not come into contact with a significant portion of the valve frame 102 and/or the inner wall of the vessel in which the valve 100 is implanted. For example, the sinus pocket 162 can help prevent adhesion between the valve leaflets 104 and the vessel wall due to the presence of a volume of blood there between.

The sinus pocket 162 can also allows for improved valve leaflets 104 dynamics (e.g., opening and closing of the valve leaflets 104). For example, the sinus pocket 162 can allow for pressure differentials across the surfaces of the valve leaflets 104 that provide for more rapid closing of the valve leaflets 104 as the retrograde blood flow begins, as will be discussed herein.

In one embodiment, the free edge 160 of the first and second valve leaflets 150, 152 is adjacent the commissure 154. In one embodiment, the free edge 160 has a surface that defines a curve 164 between the first and second openings 138, 140. The curve 164 also has a bottom 166 relative the first and second openings 138, 140. The free edge 160 can have either a non-planar or a planar configuration. As illustrated, the free edge 160 of the first and second leaflets 150, 152 define the bottom 166 of the curve 164 that is at least a predetermined distance away from the second structural member 114 so as to define the gap 158 between the first and second leaflet 150, 152 and the second structural member 114. The gap is shown in greater detail in FIGS. 9A-C.

In one embodiment, whether the free edge 160 has a planar or non-planar configuration can depend on what material is selected for forming the valve leaflets 104. For example, when a stiffer material (e.g., PTFE) is used for the valve leaflets 104 the free edge 160 can have more of a concave shape than a planar or straight shape. In other words, as illustrated in FIG. 1A, the free edge 160 transitions from a first position adjacent the first and second openings 138, 140 to a second position lower than the first position as illustrated approximately midway between the first and second openings 138, 140. So, the free edge 160 dips down to a low point approximately midway between and relative to the first and second openings 138, 140. In one embodiment, this shape allows the free edge 160 to form a catenary when the valve leaflets 104 are in their closed position, as illustrated in FIG. 1A. In an alternative embodiment, when an elastic material is used for the valve leaflets 104 the free edge 160 has more of a straight or planar shape. In other words, the free edge 160 maintains essentially the same relative position around the circumference of the valve leaflets 104.

In addition, the dimensions and configuration of the valve leaflets 104 can further include proportional relationships to structures of the valve frame 102. For example, the first and second leaflets 150, 152 can each have a predetermined length between the distal point 148 and the bottom 166 of the curve 164 that is at least fifty percent (50%) greater than a radius of the elongate base portion 116. In one embodiment, this dimensional relationship is taken when the valve leaflets 104 are in their closed position. Valve leaflet length is discussed in greater detail below with regard to FIGS. 9A-C.

In addition to allowing the valve leaflets 104 to be coupled to the valve frame 102, the valve leaflet connection location 136 can also include predetermined dimensional relationships between portions of the valve leaflet connection location 136. For example, predetermined dimensional relationships can exist between the relative positions of the first and second openings 138, 140 and the predefined portion 146 of the first structural member 112. These dimensional relationships can help to better position the valve leaflets 104 in relation to the bulbous portion 120 of the valve frame 102.

In an additional embodiment, a predetermined portion of the surfaces of the valve leaflets 150, 152 that contact to define the commissure 154 can extend parallel to the center longitudinal axis 134 of the valve 100 when the valve 100 is in its closed configuration (FIG. 1A). For example, the predetermined portion of the surfaces of the valve leaflets 150, 152 can include twenty percent (20%) of the predetermined length of the valve leaflets 150, 152 between the distal point 148 and the bottom 166 of the curve 164. In other words, at least twenty percent (20%) of the length of the valve leaflet 150, 152 surfaces contact to form the commissure 154.

As will be appreciated, the free edge 160 when the valve leaflets 104 are in their open configuration can have a non-round shape. For example, the free edge 160 can have an eye shape or an oval shape with the second axis extending between the first and second openings 138, 140. As will be appreciated, other shapes for the valve leaflets 104 in their open configuration are also possible, including a round shape.

In one embodiment, under antegrade fluid flow (i.e., positive fluid pressure) from the second end 110 towards the first end 108 of the valve 100, the valve leaflets 104 can expand toward the inner surface 170 of the bulbous portion 120 of the frame 102 to create an opening through which fluid is permitted to move. In one example, the valve leaflets 104 each expand to define a semi-tubular structure having an oval cross-section when fluid opens the commissure 154.

As discussed herein, in the open configuration the gap 158 exists between the free edge 160 of the first and second valve leaflets 150, 152 and the bulbous portion 120 of the valve frame 102. In one embodiment, the size and shape of the valve leaflets 104 provides the gap 158 thereby preventing the valve leaflets 104 from touching the vein wall.

In addition, the size and shape of the valve leaflets 104 along with the gap 158 provides for more responsive opening and closing of the commissure 154 due to hydrodynamic relationships that are formed across the valve leaflets 104. For example, as the leaflets 104 are not in contact with the vessel wall and/or the bulbous portion 120 of the frame 102, the leaflets 104 can be more responsive to changes in the flow direction. The presence of the sinus pocket 162 allows slower moving fluid (e.g., blood) to move into the pocket and faster moving blood on the flow side of the leaflet 104 to create a pressure differential. This pressure differential across the valve leaflets 104 provides for the Bernoulli effect for which an increase in fluid flow velocity there occurs simultaneously a decrease in pressure. So, as fluid flow becomes retrograde the fluid velocity through the opening of the valve leaflets 104 is larger than the fluid flow in the sinus pocket 162. As a result, there is a lower pressure in the opening of the valve leaflets 104 that causes the opening to close more quickly as compared to valves without the sinus pocket 162.

In an additional embodiment, the configuration of the present embodiments allows the leaflets 104 to experience a low shear as compared to angled leaflets which are subject to high shear and direct impact with flowing blood. This can be attributed to the alignment of the valve leaflets 104 with the elongate base portion 116, and the adjacent vein segment, above and below the sinus pocket 162. The sinus pocket 162 also allows for recirculation of blood within the pocket 162 that cleans out potential thrombus buildup in the bottom of the pocket 162.

The embodiments of the frame described herein can also be constructed of one or more of a number of materials and in a variety of configurations. The frame embodiments can have a unitary structure with an open frame configuration. The frame can also be self-expanding. Examples of self-expanding frames include those formed from temperature-sensitive memory alloy which changes shape at a designated temperature or temperature range, such as Nitinol. Alternatively, the self-expanding frames can include those having a spring-bias. In addition, the valve frame 102 can have a configuration that allows the frame embodiments be radially expandable through the use of a balloon catheter. In this embodiment, the valve frame can be provided in separate pieces (e.g., two frame pieces) that are delivered individually to the implant site.

The embodiments of the frame 102 can also be formed from one or more contiguous frame members. For example, the first and second structural member 112, 114 of the frame 102 can be formed from a single contiguous member. The single contiguous member can be bent around an elongate tubular mandrel to form the frame. The free ends of the single contiguous member can then be welded, fused, crimped, or otherwise joined together to form the frame. In an additional embodiment, the first and second structural member 112, 114 of the frame 102 can be derived (e.g., laser cut, water cut) from a single tubular segment. In an alternative embodiment, methods of joining the first and second structural member 112, 114 of the frame 102 to create the elastic region include, but are not limited to, welding, gluing, and fusing the frame member. The frame 102 can be heat set by a method as is typically known for the material which forms the frame 102.

The valve frame 102 can be formed from a number of materials. For example, the frame can be formed from a biocompatible metal, metal alloy, polymeric material, or combination thereof. As described herein, the frame can be self-expanding or balloon expandable. In addition, the frame can be configured so as to have the ability to move radially between the collapsed state and the expanded state. Examples of suitable materials include, but are not limited to, medical grade stainless steel (e.g., 316L), titanium, tantalum, platinum alloys, niobium alloys, cobalt alloys, alginate, or combinations thereof. Additional frame embodiments may be formed from a shape-memory material, such as shape memory plastics, polymers, and thermoplastic materials. Shaped memory alloys having superelastic properties generally made from ratios of nickel and titanium, commonly known as Nitinol, are also possible materials. Other materials are also possible.

The lumen 106 can include a number of sizes. For example, the size of the lumen can be determined based upon the type of body lumen and the body lumen size in which the valve is to be placed. In an additional example, there can also be a minimum value for the width for the frame that ensures that the frame will have an appropriate expansion force against the inner wall of the body lumen in which the valve is being placed.

The valve 100 can further include one or more radiopaque markers (e.g., rivets, tabs, sleeves, welds). For example, one or more portions of the frame can be formed from a radiopaque material. Radiopaque markers can be attached to, electroplated, dipped and/or coated onto one or more locations along the frame. Examples of radiopaque material include, but are not limited to, gold, tantalum, and platinum.

The position of the one or more radiopaque markers can be selected so as to provide information on the position, location and orientation (e.g., axial, directional, and/or clocking position) of the valve during its implantation. For example, radiopaque markers can be configured radially and longitudinally (e.g., around and along portions of the first structural member 112) on predetermined portions of the valve frame 102 to allow the radial and axial position of the valve frame 102 to be determined. So in one embodiment a radiograph image of the valve frame 102 taken perpendicular to the valve leaflets 104 in a first clock position can produce a first predetermined radiograph image (e.g., an imaging having the appearance of an inverted "Y") and a radiographic image taken perpendicular to the first and second openings 138, 140 in a second clock position can produce a second predetermined radiograph image (e.g., an imaging having the appearance of an upright "Y") distinguishable from the first predetermined radiograph image.

In one embodiment, the first and second predetermined radiograph images allow the radial position of the leaflets 104 to be better identified within the vessel. This then allows a clocking position for the valve 100 to be determined so that the valve can be positioned in a more natural orientation relative the compressive forces the valve will experience in situ. In other words, determining the clocking of the valve as described herein allows the valve to be radially positioned in same orientation as native valve that it's replacing and/or augmenting.

In one embodiment, the material of the valve leaflets 104 can be sufficiently thin and pliable so as to permit radially-collapsing of the valve leaflets 104 for delivery by catheter to a location within a body lumen. The valve leaflets 104 can be constructed of a fluid-impermeable biocompatible material that can be either synthetic or biologic. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), Dacron, polyethylene (PE), polyethylene terephthalate (PET), silk, Rayon, Silicone, or the like. Possible biologic materials include, but are not limited to, autologous, allogeneic or xenograft material. These include explanted veins and decellularized basement membrane materials (such as non-crosslinked bladder membrane or amnionic membrane), such as small intestine submucosa (SIS) or umbilical vein. As will be appreciated, blends or mixtures of two or more of the materials provided herein are possible. For example, SIBS can be blended with one or more basement membrane materials.

As described herein, a number of methods exist for attaching the valve leaflets 104 to the valve frame 102. For example, when positioned over the inter surface 114 of the frame 102, the valve leaflets 104 can be secured to the frame members 118 through the use of biocompatible staples, glues, sutures or combinations thereof. In an additional embodiment, the valve leaflets 104 can be coupled to the frame members 118 through the use of heat sealing, solvent bonding, adhesive bonding, or welding the valve leaflets 104 to either a portion of the valve leaflets 104 (i.e., itself) and/or the frame 102.

With respect to coupling the valve leaflets 104 to the first and second openings 138, 140 and the other portions of the valve leaflet connection location 136, the valve leaflets 104 can be passed from the inner surface 170 of the first structural member 112 and wrapped around at least a portion of the outer surface 118 adjacent the first and second openings 138, 140. For example, securing the valve leaflets 104 at the first and second openings 138, 140 can be accomplished by making longitudinal cuts of a predetermined length into the valve leaflets 104 adjacent the first and second openings 138, 140. In one embodiment, each cut creates two flaps adjacent each of the first and second openings 138, 140. The flaps can then pass through the frame adjacent the first and second openings 138, 140 and each of the two resulting flaps can be wrapped from the inner surface 170 around the frame 102 to the outer surface 118. The valve leaflets 104 can then be coupled to itself and/or the frame 102, as described herein. In addition, sutures can be passed through the first and second openings 138, 140 and the valve leaflets 104 so as to secure the valve leaflets 104 to the frame 102. In one embodiment, providing the flaps as described allows for the valve leaflets 104 to create a more fluid tight commissure 154 in the area adjacent the first and second openings 138, 140.

The valve leaflets 104 can have a variety of sizes and shapes. For example, each of the valve leaflets 104 can have a similar size and shape. Alternatively, each of the valve leaflets 104 need not have a similar size and shape (i.e., the valve leaflets can have a different size and shape with respect to each other).

In an additional embodiment, the valve leaflets 104 can include one or more support structures, where the support structures can be integrated into and/or onto the valve leaflets 104. For example, the valve leaflets 104 can include one or more support ribs having a predetermined shape. In one embodiment, the predetermined shape of the support ribs can include a curved bias so as to provide the valve leaflets 104 with a curved configuration. Support ribs can be constructed of a flexible material and have dimensions (e.g., thickness, width and length) and cross-sectional shape that allows the support ribs to be flexible when the valve leaflets 104 are urged into an open position, and stiff when the valve leaflets 104 are urged into a closed position upon experiencing sufficient back flow pressure from the direction downstream from the valve. In an additional embodiment, support ribs can also be attached to frame 102 so as to impart a spring bias to the valve leaflets in either the open or the closed configuration.

As described herein, the valve leaflets 104 can be located over at least the inner surface 170 of the frame 102. FIGS. 1A and 1B illustrate an embodiment of this configuration, where the material of the valve leaflets 104 extends over the inner surface 170 and the outer surface 118 of the first structural member 112 in the valve leaflet connection location 136, as described herein. Numerous techniques may be employed to laminate or bond the material of the valve leaflets 104 on the outer surface 118 and/or the inner surface 170 of the frame 102, including heat setting, adhesive welding, application of uniform force and other bonding techniques. The material of the valve leaflets 104 can also be joined to itself and/or the first structural member 112 according to the methods described in U.S. Patent Application Publication US 2002/0178570 to Sogard et al., which is hereby incorporated by reference in its entirety.

The material can also be coupled to the valve leaflet connection location 136 of the first structural member 112 so as to form the valve leaflets 104, as described herein. In one embodiment, the material for the valve leaflets 104 can be in the form of a sheet or a sleeve of material, as described herein, which can be connected to the frame 102. Alternatively, the material for the valve leaflets 104 can initially be in the form of a liquid that can be used to cast and/or form the valve leaflets 104 over the frame 102. Other forms, including intermediate forms, of the valve leaflets 104 are also possible.

The material of the valve leaflets 104 can be coupled to the valve leaflet connection location 136 of the first structural member 112, including the first and second openings 138, 140, in a variety of ways so as to provide the various embodiments of the valve of the present disclosure. For example, a variety of fasteners can be used to couple the material of the valve leaflets 104 to the frame 102 so as to form the valve 100. Suitable fasteners can include, but are not limited to, biocompatible staples, glues, sutures or combinations thereof. In an additional embodiment, the material of the valve leaflets 104 can be coupled to the frame 102 through the use of heat sealing, solvent bonding, adhesive bonding, or welding the material of the valve leaflets 104 to either a portion of the valve leaflets 104 (i.e., itself) and/or the frame 102.

The valve leaflets 104 may also be treated and/or coated with any number of surface or material treatments. For example, the valve leaflets 104 can be treated with one or more biologically active compounds and/or materials that may promote and/or inhibit endothelization and/or smooth muscle cell growth of the valve leaflets 104. Similarly, the valve leaflets 104 may be seeded and covered with cultured tissue cells (e.g., endothelial cells) derived from a either a donor or the host patient which are attached to the valve leaflets 104. The cultured tissue cells may be initially positioned to extend either partially or fully over the valve leaflets 104.

Valve leaflets 104 can also be capable of inhibiting thrombus formation. Additionally, valve leaflets 104 may either prevent or facilitate tissue ingrowth there through, as the particular application for the valve 100 may dictate. For example, valve leaflets 104 on the outer surface 112 may be formed from a porous material to facilitate tissue ingrowth there through, while valve leaflets 104 on the inner surface 114 may be formed from a material or a treated material which inhibits tissue ingrowth.

FIGS. 3A through 3E provide illustrations of different configurations of the valve frame 302 that have been cut to provide them in a planar view. As illustrated, the valve frame 302 includes the first and second structural members 312, 314 that form the elongate base portion 316 and the bulbous portion 320, respectively. In one embodiment, the first and second structural members 312, 314 of the elongate base portion 316 and the bulbous portion 320 can include a series of interconnected members. These interconnected members, in one embodiment, can act as spring members to help retain the expanded shape of the valve frame 302. In one embodiment, the interconnection of these members allows for the spring force of aligned springs integrated into the frame 302 to be added in series so as to increase the spring force potential of the frame 302.

As illustrated, the first and second structural members 312, 314 can have a number of different configurations that provide the elongate base portion 316 and the bulbous portion 320. As will be appreciated, other configurations are possible that provide the bulbous portion 320 and/or the elongate base portion 316. In addition, the bulbous portion 320 of the valve frame 302 can have a number of different configurations so as to provide the sinus pocket, as discussed herein. For example, the bulbous portion 320 can have one or more of a spherical, semi-spherical, oviod, semi-oviod, conical, semi-conical, torus, semi-torus, cylindrical, and semi-cylindrical. In addition, each of two or more of the sinus pockets of the valve frame 302 can have different shapes as discussed herein. In other words, the need not have the same shape as the other sinus pocket of the valve frame 302.

In addition, the first and second structural members 312, 314 can each have two or more cross-sectional shapes and/or two or more different dimensions (e.g., a greater width and depth of the first and second structural members 312, 314 for the portions of the elongate base portion 316 and/or the bulbous portion 320 as compared to the remainder of the elongate base and/or bulbous portion 316, 320.

As illustrated, the valve frame 302 can include the valve leaflet connection region 336 for coupling the valve leaflets. As discussed herein, the valve leaflet connection region 336 can include the first and second opening 338, 340 and the predetermined portion 346 of the first structural member 312.

The frame can also be described as comprising a first structural member 112, 312 that forms both ends of the valve; and a bulbous portion formed by a second structural member 114, 314 comprised of bulbous portion members engaged to and extending outward from the first structural member 112, 312. This is shown for example in FIGS. 1A-B and 3A-E.

As can be seen in FIGS. 3A-E, the first structural member 312 comprises circumferentially adjacent longitudinal segments where each longitudinal segment extends between the first end and the second end of the valve. Also, each longitudinal segment is engaged to a curve at each end of the valve. As discussed above, the free edge of the leaflet is engaged to leaflet attachment locations such as openings 338, 340 of circumferentially adjacent longitudinal segments.

Figure 3A:
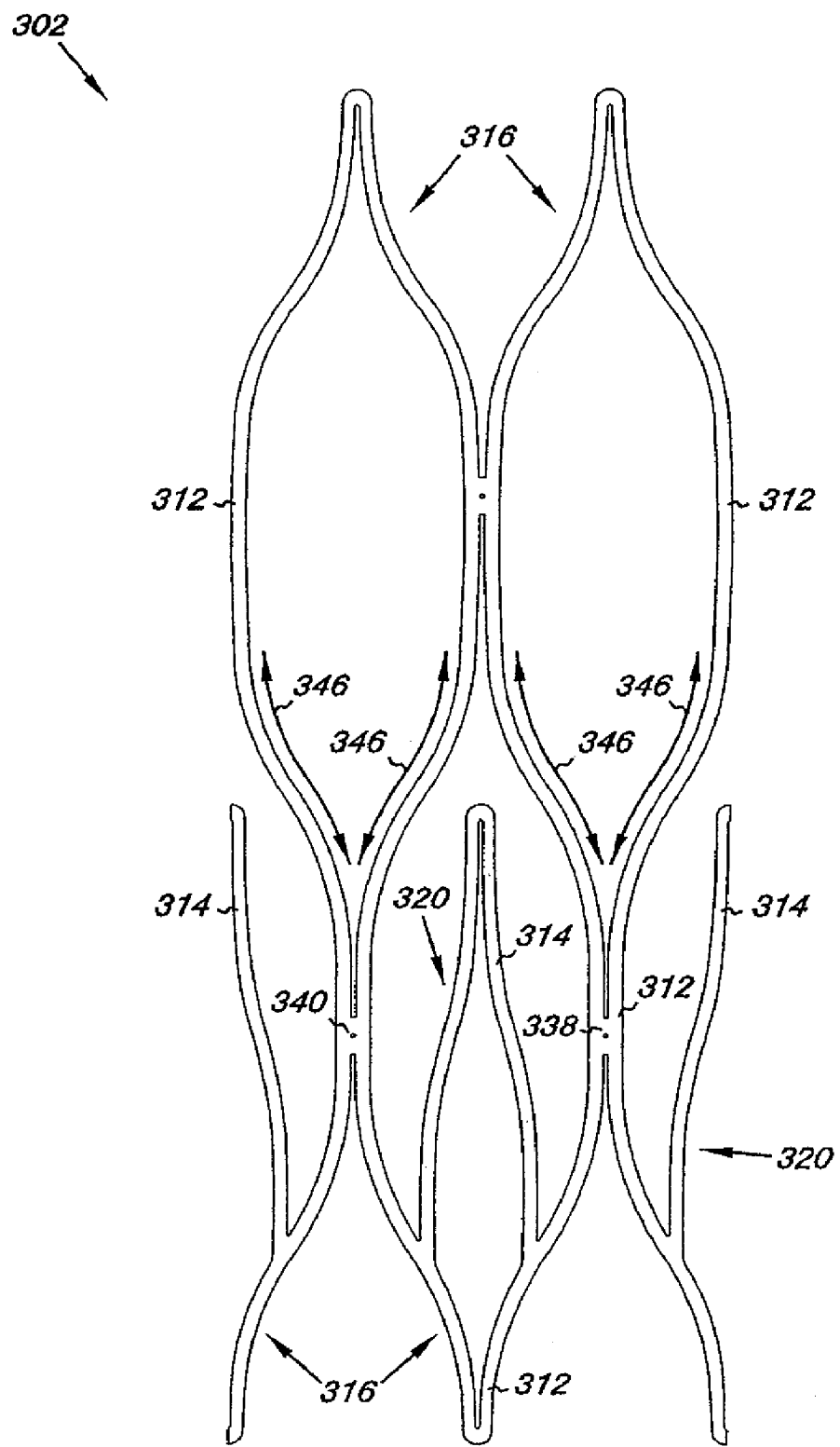
FIGS. 3A-3E illustrate embodiments of valve frame configurations according to the present disclosure.
Figure 3B:
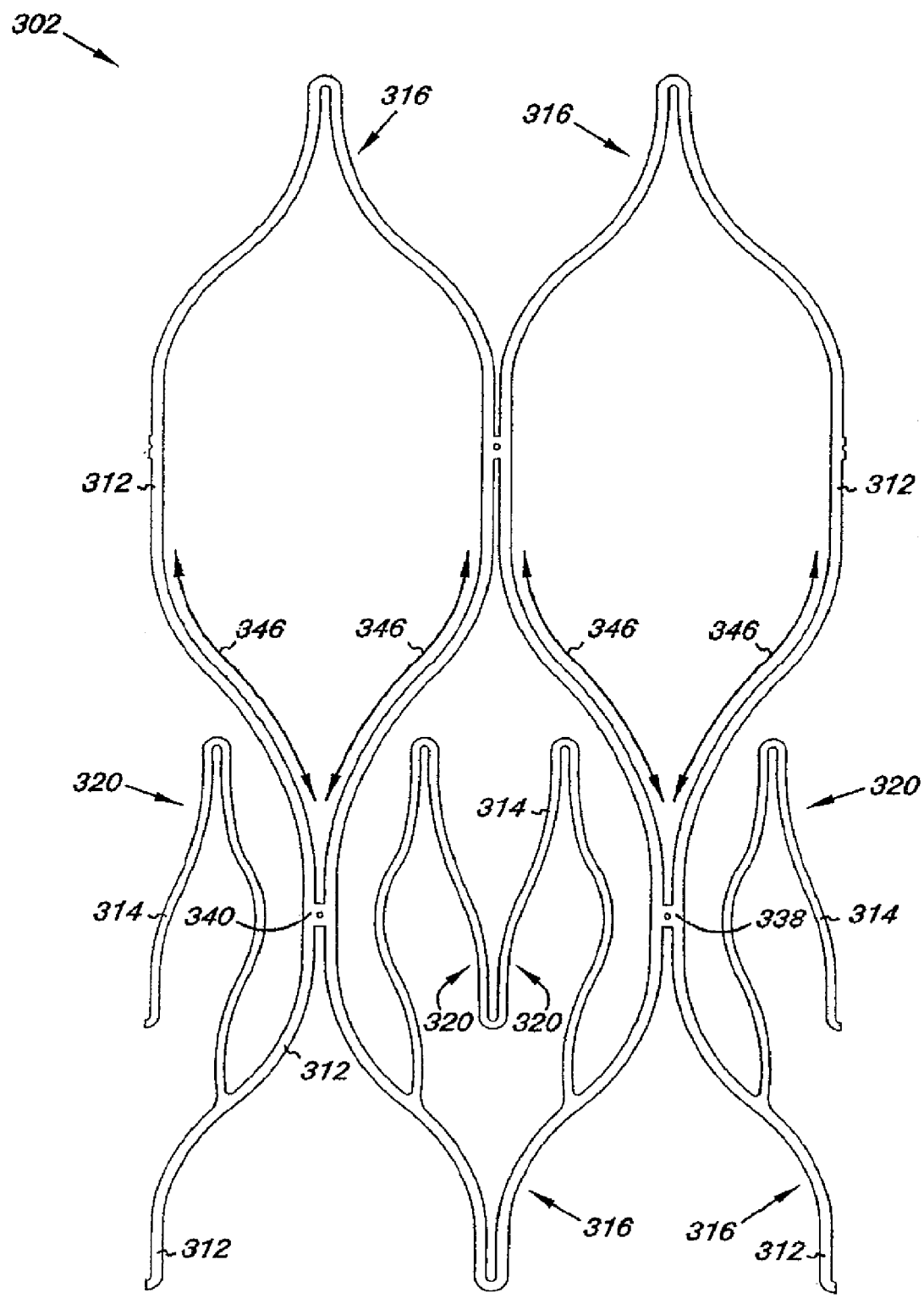
Figure 3C:
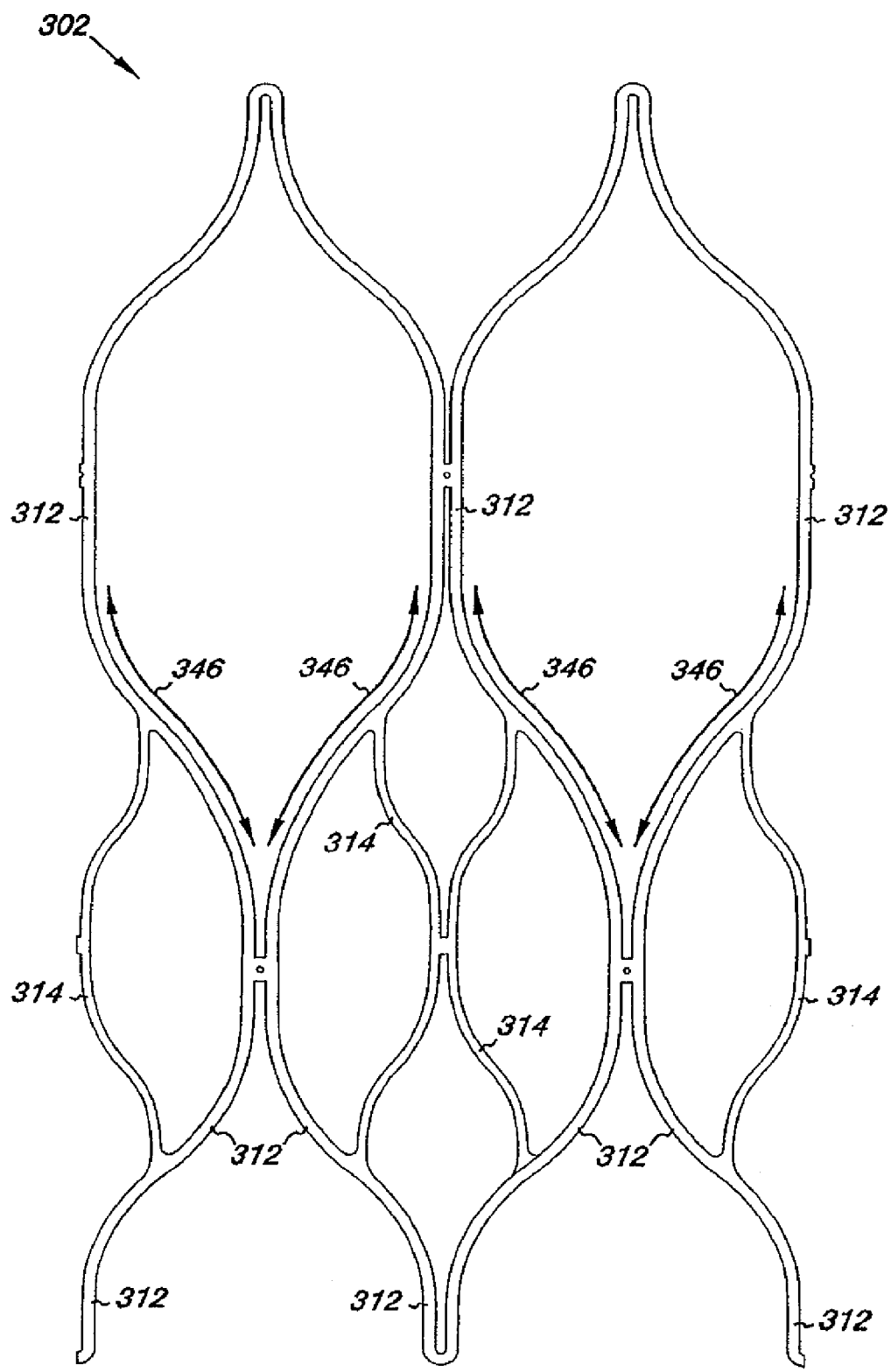
Figure 3D:
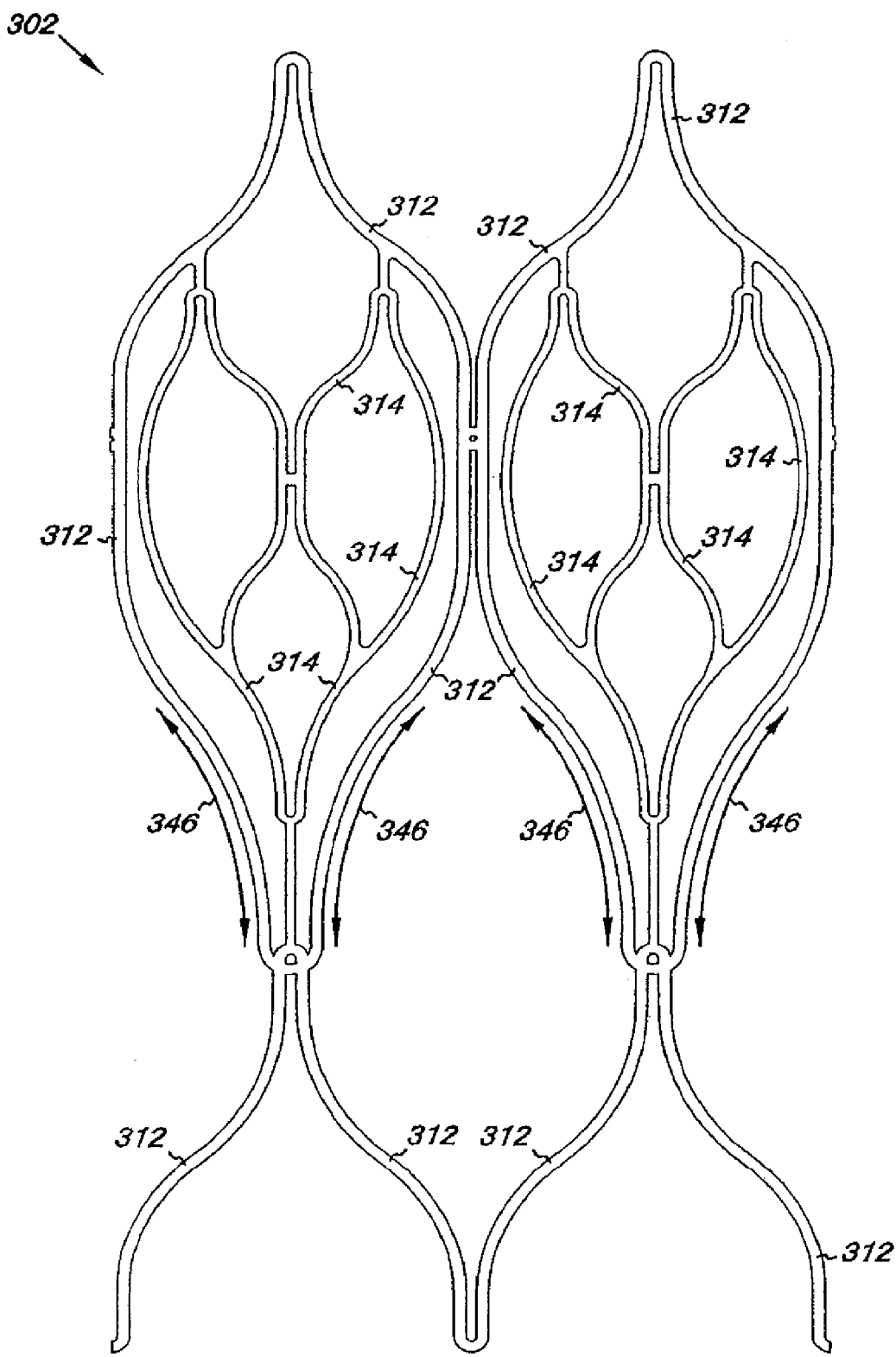
Figure 3E:
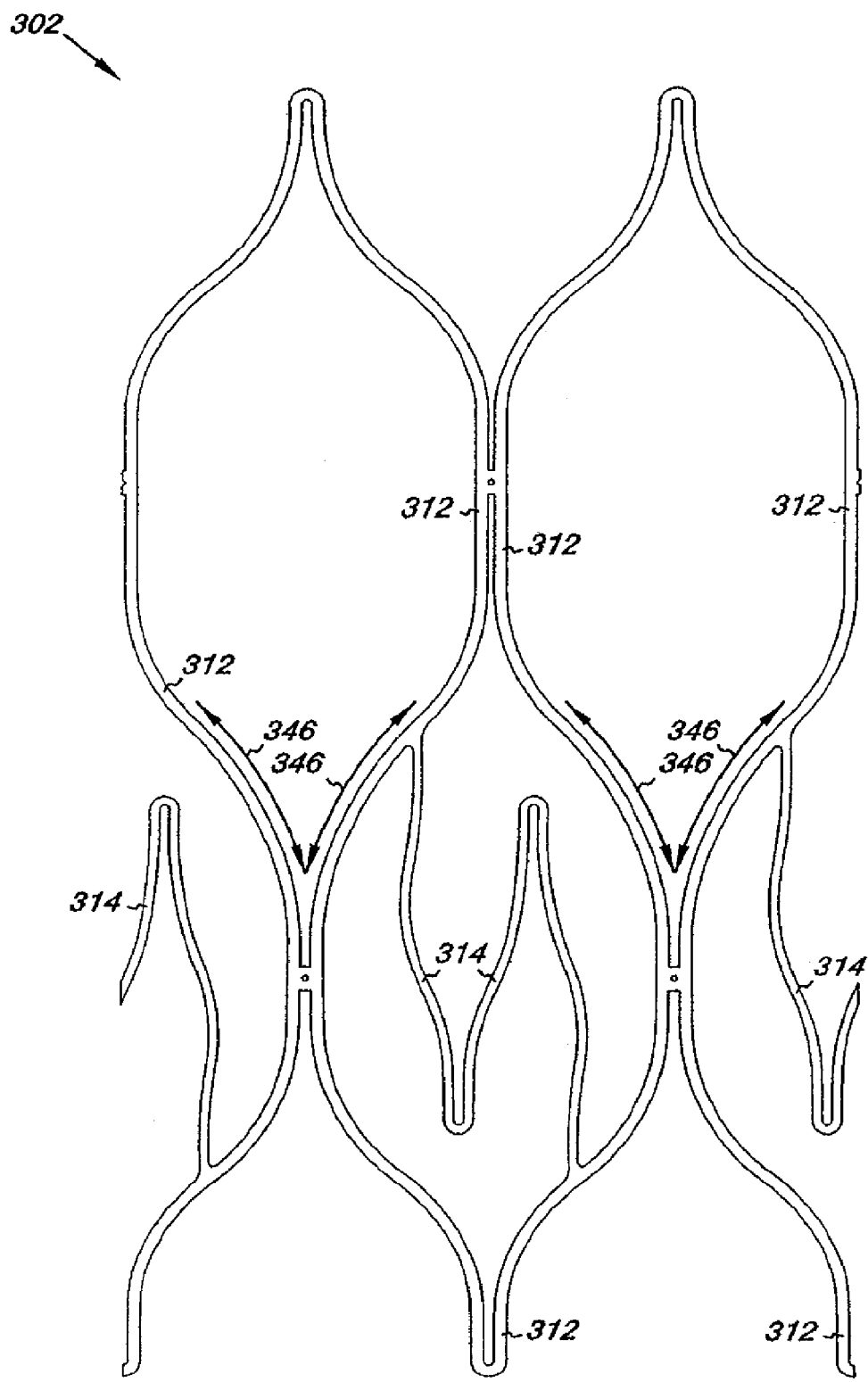

In FIGS. 3A-B, the second structural member 314 comprises two bulbous portion members. The bulbous portion member can have one turns, as shown in FIG. 3A, two turns as shown in FIG. 3E, or three turns, as shown in FIG. 3B. As shown for example in FIGS. 3A-B and E, each bulbous portion member is engaged to two circumferentially adjacent longitudinal segments of the first structural member 312.

The frame can be described as comprising a first structural member 312 forming a first zig-zag ring and a second zig-zag ring interconnected to one another by connecting segments that extend between the two zig-zag rings. This can be seen for example in FIGS. 3A-E. The connecting segments also form a zig-zag ring, as shown in FIGS. 3A-E. The zig-zag rings form the two ends of the valve. As shown in FIGS. 3A-E, each zig-zag ring forms two turns at each end of the valve. In FIGS. 3A-B, the second structural member 314 is engaged only to one of the zig-zag rings. In these embodiments, the second structural member 314 is engaged to and extends outward from the zig-zag ring. In FIGS. 3C and 3E, the second structural member 314 is engaged to one zig-zag ring and to the connecting segments. In these embodiments, the second structural member 314 is engaged to and extends outward from the zig-zag ring and from the connecting segments. In FIG. 3D, the second structural member 314 is engaged to both zig-zag rings. In these embodiments, the second structural member 314 is engaged to and extends outward from both zig-zag rings.

Figure 4:
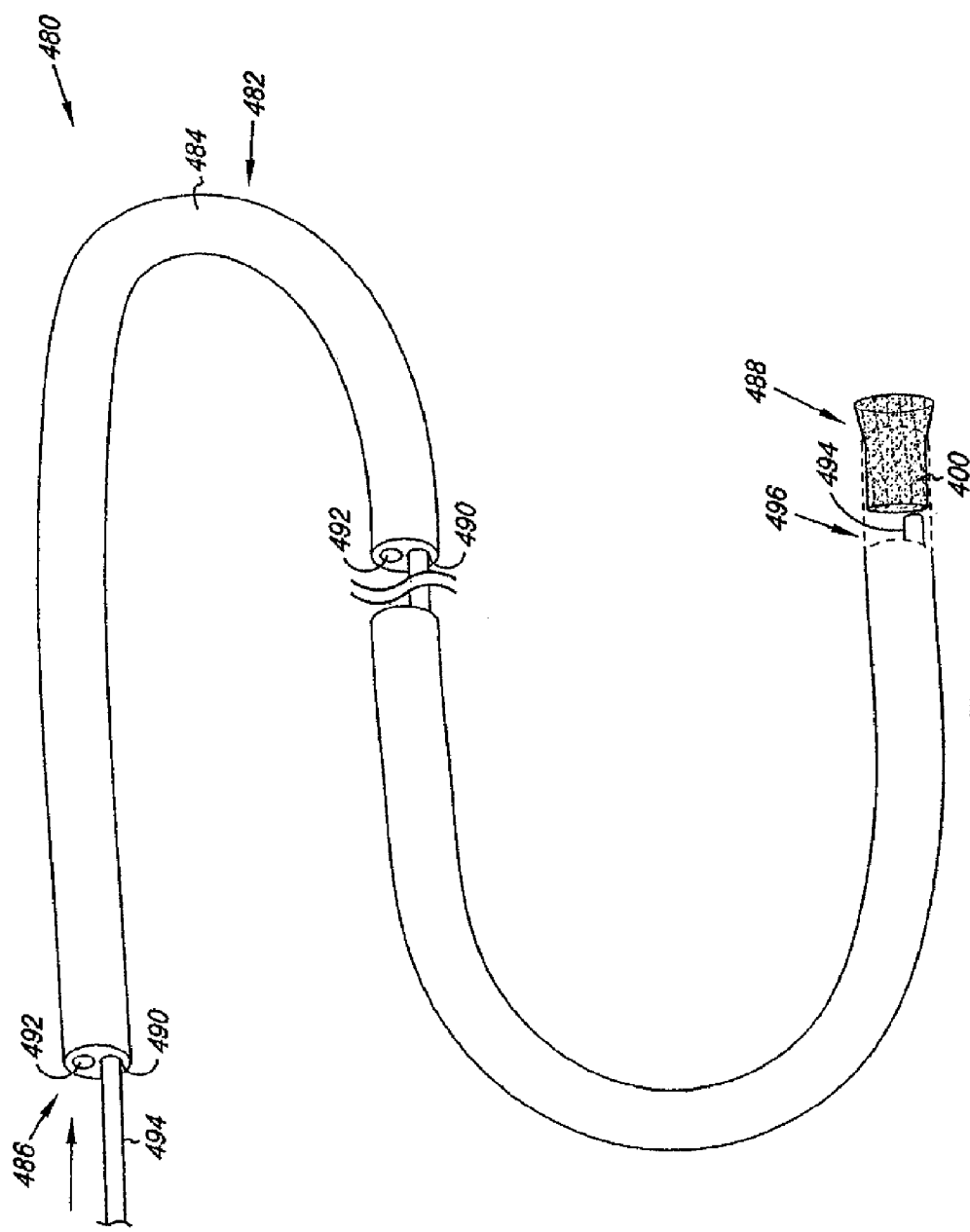
FIG. 4 illustrates an embodiment of a system that includes a valve according to the present disclosure.

FIG. 4 illustrates one embodiment of a system 480. System 480 includes valve 400, as described herein, reversibly joined to catheter 482. The catheter 482 includes an elongate body 484 having a proximal end 486 and a distal end 488, where valve 400 can be located between the proximal end 486 and distal end 488. The catheter 482 can further include a lumen 490 longitudinally extending to the distal end 488. In one embodiment, lumen 490 extends between proximal end 486 and distal end 488 of catheter 482. The catheter 482 can further include a guidewire lumen 492 that extends within the elongate body 484, where the guidewire lumen 492 can receive a guidewire for positioning the catheter 482 and the valve 400 within a body lumen (e.g., a vein of a patient).

The system 480 can further include a deployment shaft 494 positioned within lumen 490, and a sheath 496 positioned adjacent the distal end 488. In one embodiment, the valve 400 can be positioned at least partially within the sheath 496 and adjacent the deployment shaft 494. For example, the valve 400 can be fully or partially sheathed with the sheath 496. The deployment shaft 494 can be moved within the lumen 490 to deploy valve 400. For example, deployment shaft 494 can be used to push valve 400 from sheath 496 in deploying valve 400.

FIG. 5 illustrates an additional embodiment of the system 580. The catheter 582 includes elongate body 584, lumen 590, a retraction system 598 and a retractable sheath 596. The retractable sheath 596 can be positioned over at least a portion of the elongate body 584, where the retractable sheath 596 can move longitudinally along the elongate body 584. The valve 500 can be positioned at least partially within the retractable sheath 596, where the retractable sheath 596 moves along the elongate body 596 to deploy the valve 500. For example, the valve 500 can be fully or partially sheathed with the sheath 596.

In one embodiment, retraction system 598 includes one or more wires 501 coupled to the retractable sheath 596, where the wires are positioned at least partially within and extend through lumen 590 in the elongate body 584. Wires of the retraction system 598 can then be used to retract the retractable sheath 596 in deploying valve 500. In one embodiment, a portion of the elongate body 584 that defines the guidewire lumen 592 extends through the lumen 506 of the valve 500 to protect the valve 500 from the movement of the guidewire 509.

Figure 6A:
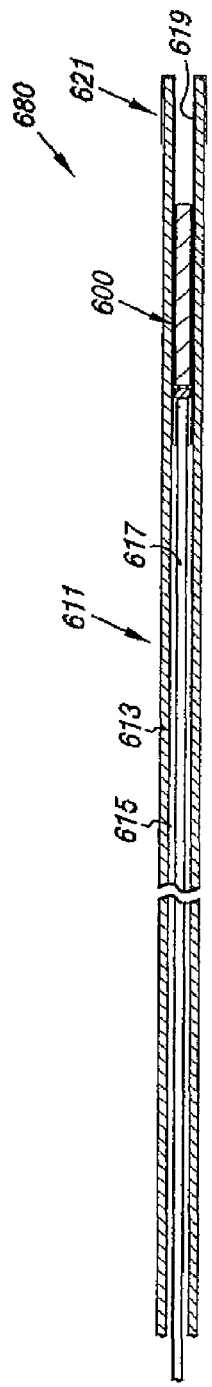
FIGS. 6A, 6B and 6C illustrate an embodiment of a system that includes a valve according to the present disclosure.
Figure 6B:
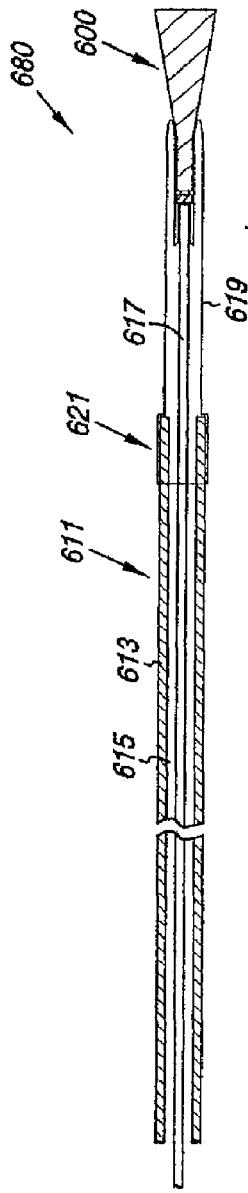
Figure 6C:
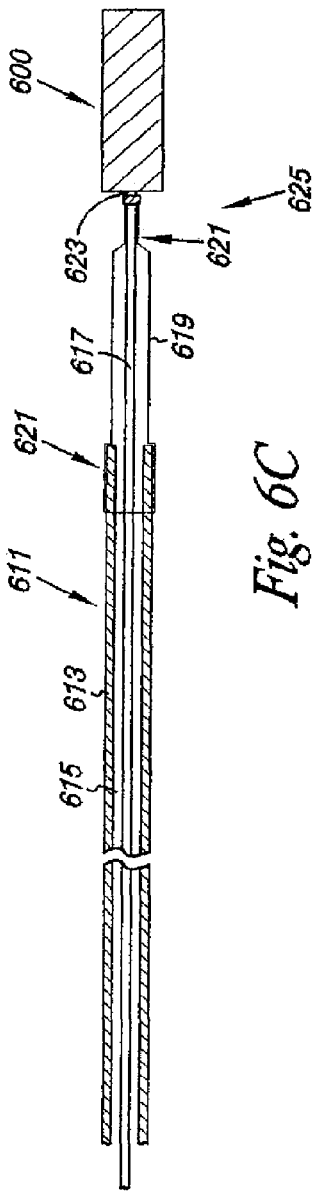

FIGS. 6A-6C illustrate an additional embodiment of the system 680. The system 680 includes a tubular sheath 611 having an elongate body 613 and a lumen 615. The system 680 further includes a delivery shaft 617 positioned within the lumen 615 of the tubular sheath 611. In one embodiment, the tubular sheath 611 and the delivery shaft 617 can move longitudinally relative each other.

In one embodiment, the system 680 includes a flexible cover 619 between the tubular sheath 611 and the delivery shaft 617. In one embodiment, the flexible cover 619 is connected to the tubular sheath 611 and the delivery shaft 617 at a fluid tight seal 621 so as to prevent the transmission of friction from the elongate body 613 to device 600 while the elongate body 613 is retracted during the deployment cycle. In one embodiment, this can be accomplished by creating intentional friction surfaces between the elongate body 613 and flexible cover 619 as is demonstrated in FIG. 6A or two layers of the flexible cover 619 as is demonstrated in FIG. 6B.

In one embodiment, the tubular sheath 611, the delivery shaft 617 and the flexible cover 619 can each be formed from a number of different materials. For the tubular sheath examples include, but are not limited to materials selected from one or more of ePTFE, PTFE, PE, PET, silicone, and polyurethanes. For the delivery shaft 617 examples include, but are not limited to, those selected from a metal, a metal alloy, and/or a polymer. Examples include, but are not limited one or more of ePTFE, PTFE, PE, nylons, PET, silicone, polyurethanes, and stainless steel (e.g., 316L).

In addition, the delivery shaft 617 can also include a configuration that imparts sufficient column rigidity to allow it to be pushed and/or pulled through the lumen 615. For example, the delivery shaft 617 can be formed with reinforcing members bound within the body of the delivery shaft 617 (e.g., an elongate braid of stainless steel co-extruded with a polymer). For the flexible cover 619 examples include, but are not limited to, materials selected from one or more of ePTFE, PTFE, PE, PET, nylons, and polyurethanes. As will be appreciated, other materials and configurations for forming the tubular sheath 611, the delivery shaft 617 and the flexible cover 619 are also possible.

As illustrated in FIGS. 6A-6C, the valve 600 can be positioned over the delivery shaft 615 adjacent a distal end 623 of the delivery shaft 617. In addition, the valve 600 can be held in the same relative location 625 as it is being deployed. As illustrated in FIG. 6A, the valve 600, a portion of the flexible cover 619 and the delivery shaft 617 can be positioned within the lumen 615 of the tubular sheath 611. In one embodiment, the configuration illustrated in FIG. 6A allows the valve 600 to be delivered in its compressed state to a predetermined location in the lumen of the body. Once at the predetermined location, the sheath 611 can then be moved relative the delivery shaft 617. FIG. 6B illustrates a situation where the sheath 611 has been pulled over the valve 600 location 625 and at least partially over the delivery shaft 617.

As illustrated, the flexible cover 619 has a tubular configuration that folds back inside of itself (i.e., its lumen) as the tubular sheath 611 is drawn over the valve 600 and the delivery shaft 617. In one embodiment, the lumen 615 of the sheath 611 can contain a lubricating fluid (e.g., saline) to allow the flexible cover 619 to more easily pass over itself as illustrated. As the tubular sheath 611 continues to be pulled back relative the delivery shaft 617 until the valve 600 is released, as illustrated in FIG. 6C. In one embodiment, the valve 600 can include a self-expanding frame that allows the valve 600 to deploy at location 625 once released.

Figure 7A:
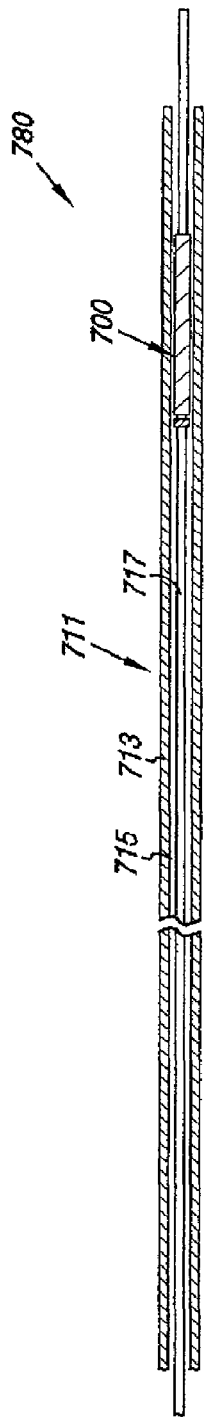
FIGS. 7A, 7B and 7C illustrate an embodiment of a system that includes a valve according to the present disclosure.
Figure 7B:
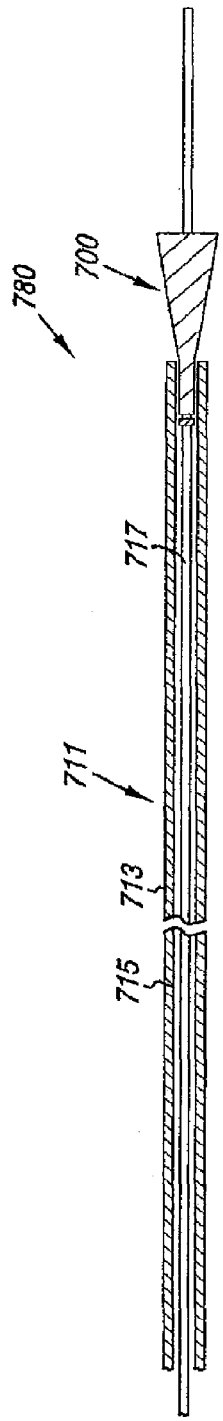
Figure 7C:
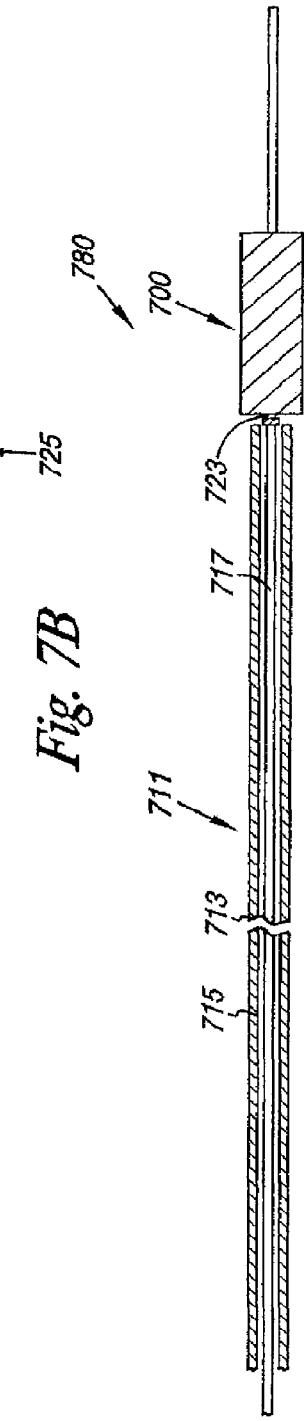

FIGS. 7A-7C illustrate an additional embodiment of the system 780. The system 780 includes a tubular sheath 711 having an elongate body 713 and a lumen 715. The system 780 further includes a delivery shaft 717 positioned within the lumen 715 of the tubular sheath 711. In one embodiment, the tubular sheath 711 and the delivery shaft 717 can move longitudinally relative each other. In contrast to the system illustrated in FIGS. 6A-6C, however, the system 780 does not include the flexible cover. As a result, the illustrated embodiment of system 780 allows for an increase in the size of the inner diameter of the elongate body 713 to be used by the delivery shaft and/or the valve 700 as compared to the elongate body that includes the flexible cover.

In one embodiment, the tubular sheath 711 and the delivery shaft 717 can each be formed from materials and have configurations as discussed herein for FIGS. 6A-6C. As illustrated in FIGS. 7A-7C, the valve 700 can be positioned over the delivery shaft 715 adjacent a distal end 723 of the delivery shaft 717. In addition, the valve 700 can be held in the same relative location 725 as it is being deployed. As illustrated in FIG. 7A, the valve 700 and the delivery shaft 717 can be positioned within the lumen 715 of the tubular sheath 711. In one embodiment, the configuration illustrated in FIG. 7A allows the valve 700 to be delivered in its compressed state to a predetermined location in the lumen of the body. Once at the predetermined location, the sheath 711 can then be moved relative the delivery shaft 717. FIG. 7B illustrates a situation where the sheath 711 has been pulled at least partially over the valve 700 at location 725 and at least partially over the delivery shaft 717. As the tubular sheath 711 continues to be pulled back relative the delivery shaft 717 the valve 700 is released, as illustrated in FIG. 7C. In one embodiment, the valve 700 can include a self-expanding frame that allows the valve 700 to deploy at location 725 once released.

The embodiments of the present disclosure further include methods for forming the valve of the present disclosure, as described herein. For example, the valve frame can be formed in a number of different ways. In one embodiment, the valve frame can be formed by cutting a tube of material so as to form the first structural member into the elongate base portion and/or the second structural member into the bulbous portion of the valve frame. Examples of techniques for cutting include laser cutting and/or water jet cutting. Other cutting techniques are also possible. When the first structural member and the second structural member are formed separately, the two portions can be joined by a welding technique, such as laser welding. Other welding or bonding techniques are also possible.

Forming the second structural member into the bulbous portion that radially and longitudinally extends from the first structural member can be accomplished through a variety of techniques. For example, the tube of material that is cut to form the first and second structural members can either be formed with or have a bulbous portion bent into the tube of material. In other words, the tube has the bulbous portion before cutting out the first and second structural members.

Alternatively, the first and second structural members can be cut from the tube. The bulbous portion can then be bent into the second structural members of the valve frame to form the bulbous portion. As discussed herein, forming the bulbous portion can include shaping the first structural member and the second structural member into a predetermined shape, such as elliptical or round. Other shapes for the bulbous portion are also possible.

The valve frame can then be positioned over a mandrel having surfaces that support the elongate base portion and the bulbous portion of the valve frame. Once positioned, the valve frame can then be processed according to the material type used for the frame. For example, the valve frame can be heated on the mandrel to set the shape of the valve frame according to techniques as are known.

The method also includes providing the material in predefined shapes for the valve leaflets. The valve leaflet material is applied and coupled to the valve leaflet connection location of the valve frame, as discussed herein, to provide at least the first leaflet and the second leaflet of the valve having surfaces defining the reversibly sealable opening for unidirectional flow of a liquid through the valve. In one embodiment, the opening defined by the valve leaflets can be configured, as discussed herein, to create a Bernoulli Effect across the valve leaflets.

In one embodiment, coupling the material of the valve leaflets to the valve frame includes locating the free edge of the valve leaflets adjacent the bulbous portion to provide both the gap and the sinus pocket between the bulbous portion in the valve frame and the valve leaflets. As discussed herein, coupling the material of the valve leaflets to the valve frame can include configuring the valve leaflets such that at least the gap between the free edge of the valve leaflets and the bulbous portion in the valve frame is maintained as the valve leaflets cycles between their opened and closed position.

In an additional example, the valve can be reversibly joined to the catheter, which can include a process of altering the shape of the valve from a first shape, for example an expanded state, to the compressed state, as described herein. For example, the valve can be reversibly joined with the catheter by positioning valve in the compressed state at least partially within the sheath of the catheter. In one embodiment, positioning the valve at least partially within the sheath of the catheter includes positioning the valve in the compressed state adjacent the deployment shaft of the catheter. In an another embodiment, the sheath of the catheter functions as a retractable sheath, where the valve in the compressed state can be reversibly joined with the catheter by positioning the valve at least partially within the reversible sheath of the catheter. In a further embodiment, the catheter can include an inflatable balloon, where the balloon can be positioned at least partially within the lumen of the valve, for example, in its compressed state.

The embodiments of the valve described herein may be used to replace, supplement, or augment valve structures within one or more lumens of the body. For example, embodiments of the present disclosure may be used to replace an incompetent venous valve and help to decrease backflow of blood in the venous system of the legs.

In one embodiment, the method of replacing, supplementing, and/or augmenting a valve structure can include positioning at least part of the catheter including the valve at a predetermined location within the lumen of a body. For example, the predetermined location can include a position within a body lumen of a venous system of a patient, such as a vein of a leg.

In one embodiment, positioning the catheter that includes the valve within the body lumen of a venous system includes introducing the catheter into the venous system of the patient using minimally invasive percutaneous, transluminal catheter based delivery system, as is known in the art. For example, a guidewire can be positioned within a body lumen of a patient that includes the predetermined location. The catheter, including valve, as described herein, can be positioned over the guidewire and the catheter advanced so as to position the valve at or adjacent the predetermined location.

As described herein, the position of the one or more radiopaque markers can be selected so as to provide information on the position, location and orientation (e.g., axial, directional, and/or clocking position) of the valve during its implantation.

For example, radiopaque markers can be configured radially and longitudinally on predetermined portions of the valve frame and/or the elongate body of the catheter to indicate not only a longitudinal position, but also a radial position of the valve leaflets and the valve frame (referred to as a clock position). In one embodiment, the radiopaque markers are configures to provide radiographic images that indicate the relative radial position of the valve and valve leaflets on the catheter.

Figure 8A:
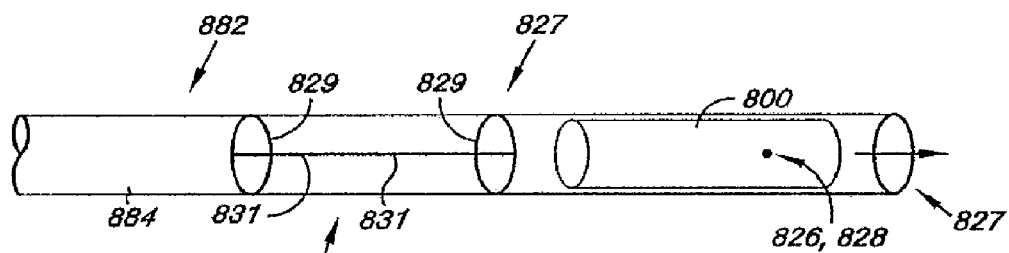
FIGS. 8A, 8B and 8C illustrate an embodiment of a system that includes a valve and a catheter having radiopaque markers according to the present disclosure.
Figure 8B:
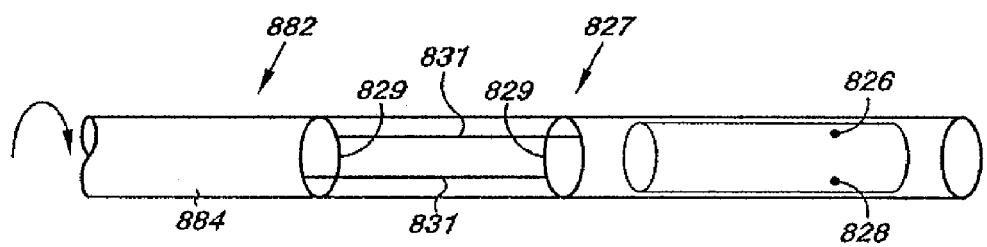
Figure 8C:
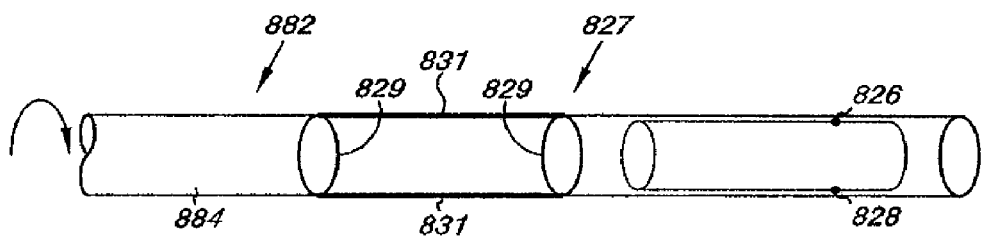

FIGS. 8A-8C provide an illustration of the radiopaque markers 827 associated with the elongate body 884 of the catheter 882. As illustrated, the radiopaque markers 827 include a radial component 829 and a longitudinal component 831. Depending upon the radial position of the catheter 882, the radiopaque markers 827 can provide a different and distinguishable radiographic image. For example, in a first position 833 illustrated in FIG. 8A the longitudinal component 831 of the radiopaque markers 827 are aligned so as to overlap. As the catheter 882 is rotated, as illustrated in FIGS. 8B and 8C, the radiographic image of the radial component 829 and/or longitudinal component 831 of the radiopaque markers 827 changes.

The change in the relationship of the radial and longitudinal components 829, 831 as the catheter 882 is rotated allows for the relative position of the valve 800, valve frame and valve leaflets to be determined from the radiographic image. For example, the relative position of the first and second leaflet connection regions 826, 828 could be aligned with longitudinal component 831 of the radiopaque markers 827. This would allow the clock position for the valve 800 to be determined so that the valve can be positioned in a more natural orientation relative the compressive forces the valve will experience in situ. In other words, the allowing for clocking of the valve 800 as described herein allows the valve to be radially positioned in same orientation as native valve that it's replacing and/or augmenting.

As will be appreciated, other relative relationships between the radiopaque markers 827 and the position of the valve 800 on the catheter 882 are possible. So, embodiments of the present disclosure should not be limited to the present example. For example, additional radiopaque markers 827 on the valve 800 could be used either alone or in combination with radiopaque markers 827 on the catheter 882 to help in positioning the valve 800 within a lumen.

The valve can be deployed from the catheter at the predetermined location in a number of ways, as described herein. In one embodiment, valve of the present disclosure can be deployed and placed in a number of vascular locations. For example, valve can be deployed and placed within a major vein of a patient's leg. In one embodiment, major veins include, but are not limited to, those of the peripheral venous system. Examples of veins in the peripheral venous system include, but are not limited to, the superficial veins such as the short saphenous vein and the greater saphenous vein, and the veins of the deep venous system, such as the popliteal vein and the femoral vein.

As described herein, the valve can be deployed from the catheter in a number of ways. For example, the catheter can include the retractable sheath in which valve can be at least partially housed, as described herein. Valve can be deployed by retracting the retractable sheath of the catheter, where the valve self-expands to be positioned at the predetermined location. In an additional example, the catheter can include a deployment shaft and sheath in which valve can be at least partially housed adjacent the deployment shaft, as described herein. Valve can be deployed by moving the deployment shaft through the catheter to deploy valve from the sheath, where the valve self-expands to be positioned at the predetermined location. In an additional embodiment, the valve can be deployed through the use of an inflatable balloon.

Once implanted, the valve can provide sufficient contact and expansion force against the body lumen wall to prevent retrograde flow between the valve and the body lumen wall. For example, the valve can be selected to have a larger expansion diameter than the diameter of the inner wall of the body lumen. This can then allow valve to exert a force on the body lumen wall and accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

In addition, the use of both the bulbous portion and/or elongate base portion of the valve can provide a self centering aspect to valve within a body lumen. In one embodiment, the self centering aspect resulting from the bulbous portion and/or elongate base portion of the valve may allow valve to maintain a substantially coaxial alignment with the body lumen (e.g., such as a vein) as valve leaflets deflect between the open and closed configurations so as to better seal the reversible opening when valve is closed.

Figure 9A:
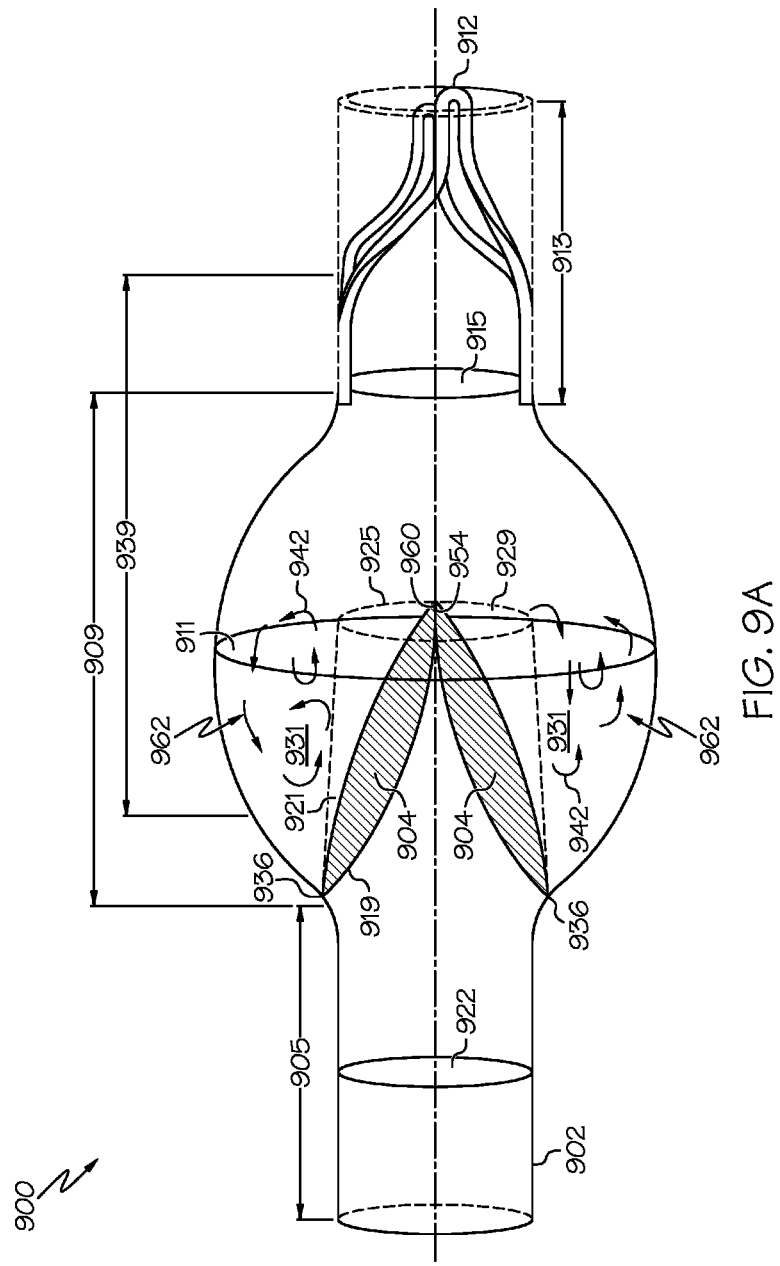
FIG. 9A illustrates the valve of the present disclosure.

Additional aspects of the valves shown FIGS. 1-3E are discussed with reference to FIGS. 9A-C. FIG. 9A provides a top view of the valve 900 with a frame 902 being generally shown as a tubular body. While frame 902 is shown as a tubular body for illustrative purposes, the present disclosure contemplates that the frame 902 can have a number of different structural configurations that will be more fully discussed herein.

The frame 902 can have an inlet region 905 that defines an inlet cross sectional area 922, a middle region 909 that defines a middle cross sectional area 911, and an outlet region 913 that defines an outlet cross sectional area 915. As will be more fully discussed herein, various embodiments provide that the inlet cross-sectional area 922 can have a different relative size than the middle cross sectional area 911. In addition, the inlet cross sectional area 922 can be at least approximately equal to the outlet cross sectional area 915. Other relative relationships, as discussed herein, are also possible.

The valve 900 also includes valve leaflets 904 at least partially connected to the frame 902. The valve leaflets 904 include a first inflow surface 919, a first outflow surface 921 opposite the first inflow surface 919 and a free edge 960. In one embodiment, the valve leaflets 904 are configured to shift between an open position, shown with a broken line 925 in FIG. 9A, and a closed position. The free edge 960 of the valve leaflet 904 helps define a free edge cross sectional area 929.

The material of the valve leaflets 904 can be connected to the frame 902 in a variety of ways so as to provide the various embodiments of the valve 900 of the present disclosure. For example, a variety of fasteners can be used to couple the material of the valve leaflets 904 to the frame 902 so as to form the valve 900. Suitable fasteners can include, but are not limited to, biocompatible staples, glues, sutures, or combinations thereof. In an additional embodiment, the material of the valve leaflets 904 can be coupled to the frame 902 through the use of heat sealing, solvent bonding, adhesive bonding, or welding the material of the valve leaflets 904 to either a portion of the valve leaflets 904 (i.e., itself) and/or the frame 902.

As illustrated in FIG. 9A, the valve leaflets 904 can be coupled to at least a portion of the valve frame 902. As illustrated, the valve leaflets 904 can move relative the valve frame 902. The valve leaflets 904 can be unbound (i.e., unsupported) by the frame 902 and can extend between opposite sides of the frame 902 in the middle region 974. This configuration permits the valve leaflets 904 to move (e.g., pivot) relative the opposite sides of the frame 902 in the middle region 909 to allow a commissure 954 to reversibly open and close for unidirectional flow of the liquid through the valve 900.

Valve provides an embodiment in which the surfaces defining the commissure provide a bi-leaflet configuration (i.e., a bicuspid valve) for valve. Although the embodiments illustrate and describe a bi-leaflet configuration for the valve of the present disclosure, designs employing a different number of valve leaflets (e.g., tri-leaflet valve) may be possible. For example, additional connection points (e.g., three or more) could be used to provide additional valve leaflets (e.g., a tri-leaflet valve).

In addition, embodiments of the present disclosure couple the valve leaflets 904 to the frame 902 in a way such that the valve leaflets 904 in the closed position form a fluid tight commissure 954.

The relationship between the valve leaflets 904 and the frame 902 also help to define a sinus region 962. As illustrated, the sinus region 962 can be defined by a volume 931 between the frame 902 and the valve leaflets 904 extending from an attachment location 936 to the free edge 960 while in the open position. As shown in FIG. 1A, the attachment location is the distal point 148 of the predefined portion 146 of the first structural member 112 to which the leaflet is engaged.

In one embodiment, the sinus region 962 can perform a variety of functions for the valve 900. For example, the sinus region 962 can allow for blood moving through the valve 900 to backwash into and through the sinus region 962. While not wishing to be bound by theory, the formation of the backwash into and through the sinus region 962 is a result of a separation of the blood flow as it moves past the free edge 960 of the valve leaflets 904. Separation occurs due to the extreme change in cross sectional area as the blood emerges from the free edge cross-sectional area 929 into the area defined by the middle cross-section 976. This separation forms eddy currents 942 that wash back into the sinus region 962 keeping both constant blood flow through the sinus region 962 and separating the valve leaflets 904 from the frame 902 and the native vessel wall. This latter feature helps to minimize the likelihood that the valve leaflets 904 will adhere to the frame 902 and/or any of the native vessel wall in which the valve 900 is placed.

The sinus region 962 also allows for improved valve leaflet 904 dynamics (e.g., opening and closing of the valve leaflets). For example, the sinus region 962 can allow for pressure differentials across the surfaces of the valve leaflets 904 that provide for more rapid closing of the valve leaflets 904 as the retrograde blood flow begins, as will be discussed herein.

As discussed herein, the presence of the sinus region 962 allows slower moving blood (e.g., backwash) to move into the sinus region 962 and faster moving blood on the first inflow surface 919 to create a pressure differential. This pressure differential across the valve leaflets 904 provides for a Bernoulli effect. The Bernoulli principle provides that the sum of all forms of energy in a fluid flowing along an enclosed path (e.g., the venous valve 900 positioned within a vein) is the same at any two points in that path. As discussed herein, the velocity of blood flow across the first inflow surface 919 of the valve leaflets 904 is greater than the velocity of blood flow across the outflow surface 921 of the valve leaflets 904. The result is a larger fluid pressure on the outflow surface 921 as compared to the first inflow surface 919. So, when blood flow slows through the valve, the fluid pressure on the first outflow surface 921 becomes larger than the fluid pressure on the first inflow surface 919 and the valve leaflets 904 have a natural tendency to "shut."

The valve leaflets 904 of the present disclosure are also configured to include a complex curvature which can be utilized to form a pocket when the valve 900 is in the closed position. The pocket is shaped synergistically to enhance the performance of the valve 900 with the sinus region 962, as discussed herein. As used herein, "pocket" means a portion of the valve leaflet 904 that is concave when in the closed position and distends when in the open position 925. For example, as discussed above region 156 of the leaflets moves relative to the frame. As can be seen in FIGS. 1A-B, the region is concave when in the closed position and distends when in the open position.

In one embodiment, the free edge 960 of the valve leaflets 904 can be positioned at a predetermined location 939 along the middle region 909 of the frame 902. For example, the predetermined location 939 can be positioned approximately at the maximum dimension of the middle cross section 909. Other predetermined locations 939 include those in the middle region 974 that are closer to the inlet region 905 than the outlet region 913. Other predetermined locations 939 are also possible, as will be discussed herein. In addition, specific dimensional relationships for the valve leaflets 904 and the middle region 909 of the frame 902 exist. These relationships will be discussed more fully herein.

According to the present disclosure, there are a variety of relative sizes for the inlet region 905, the middle region 909, and the outlet region 913 in association with the valve leaflets 904 that can provide for the backwash function of the sinus region 962. For example, as illustrated in FIG. 9A, the inlet cross-sectional area 922, the free edge cross-sectional area 929 of the valve leaflets 904 in their open position, and the outlet cross-sectional area 915 all have approximately the same cross sectional area, whereas the middle cross-sectional area 911 has a larger relative cross sectional area. For example, in one embodiment, the relative diameters of the inlet region 905, middle region 909, and outlet region 913 are approximately equal to 1.0, 1.8, and 1.1, respectively. So, as blood flows past the free edge 960 of the valve leaflets 904, the blood flow separates, forming eddy currents 942 that provide at least in part, the backwash in the sinus region 962.

In an alternative embodiment, other configurations of the comparative sizes of the inlet, middle, free edge, and outlet cross-sectional areas 922, 911, 929, and 915 are possible that can provide for the backwash function of the sinus region 962. For example, both the middle and outlet cross-sectional areas 911, 915 can be larger than both the inlet cross-sectional area 922 and the free edge cross-sectional area 929 in its open position. In an alternative embodiment, the middle cross-sectional area 911 and the free edge cross-sectional area 929 in its open position can be smaller than both the inlet and the outlet cross-sectional areas 922, 915. In yet another embodiment, the free edge cross-sectional area 929 in its open position is smaller than both the middle and outlet cross-sectional areas 911, 915 while both the middle and outlet cross-sectional areas 911, 915 are smaller than the inlet cross-sectional area 922.

In the embodiments where the free edge cross-sectional area 929 in its open position is smaller than the inlet cross-sectional area 922, the Bernoulli principle, as discussed herein, provides that the fluid velocity increases as a result of the decrease in cross-sectional area. In these embodiments, the resulting increase in fluid velocity can provide enhanced recirculation and less thrombosis throughout the valve 900 due to increased blood flow velocity that effectively "flushes" thrombus and/or other material through and out of the valve 900. Additionally, in embodiments where the middle cross-sectional area 911 is smaller than the body lumen and the free edge cross-sectional area 929 in its open position is smaller than the inlet cross-sectional area 922, an increase in fluid velocity may help to "draw in" the tissue of the native vessel wall, creating a more fluid tight position for the valve 900 of the present disclosure. On the other hand, in these embodiments a prosthetic material can be provided to the treatment site to create a narrowing where the middle cross-sectional area 911 is to be positioned.

The free edge 960 of the valve leaflets 904 in their open configuration can define a number of different shapes, including round and non-round shapes. For example, the free edge 960 can define an eye shape or an oval shape. As will be appreciated, other shapes for the valve leaflets 904 in their open configuration are also possible.

In addition, the valve leaflets 904 are illustrated as being essentially of the same size and relative shape. This allows for a symmetrical configuration for the valve leaflets 904. Alternatively, the valve leaflets 904 can have a non-symmetrical configuration, where one of the valve leaflets 904 has at least one of a different size and/or shape as compared to another of the valve leaflets 904.

As illustrated, the frame 902 is shown having a circular peripheral shape. Other peripheral shapes for the frame 902 are possible. For example, peripheral shapes for the frame 902 can include not only circular, but elliptical, obround, conical, semi-conical, semi-spherical, polygonal, or combinations thereof. In one embodiment, polygonal shapes can include those defined generally with the structural members to form, for example, triangular, tetragon (e.g., square or rectangular), pentagon, hexagon, and heptagon, among other polygonal shapes. Different combinations of these shapes for different regions 905, 909, and 913 are also possible.

Although the frame 902 can have many peripheral shapes including polygonal shapes, the functional shape of the frame 902 may change over time. For example, once the valve 900 is inserted into a body vessel, the body vessel wall will begin to form tissue deposits as it heals in and around the valve 900. As this occurs, the polygonal shape of the frame 902 may functionally change into more of a circular shape. Embodiments of the present disclosure take this process into account however, and remain functional despite potential in growth into the valve 900.

There are many ways in which the frame may be formed. As discussed above with regard to FIGS. 1A-3E, the frame includes structural members 112, 114 that define openings through the frame. FIG. 9A partially shows the structural members of the frame 902, in particular the first structural member 912. As discussed herein, the frame is shown as a tubular body for illustrative purposes; in addition, the first structural member 912 as shown in the outlet region 113 are for illustrative purposes and are not meant to limit the configuration of the frame formed by the first structural member 912.

As discussed above, in one embodiment, the structural members of frame 902 are formed by cutting the openings in a contiguous tube of material to form the inlet, the middle, and the outlet regions 905, 909, 911 of the frame 902. Examples of techniques for cutting include laser cutting and/or water jet cutting. Other cutting techniques are also possible.

Different shapes and sizes for the regions 905, 909, and 913 can then be formed by stretching and/or deforming the structural members to the desired shape and size. In one embodiment, the frame can be positioned over a mandrel that defines the desired shape of the frame. Once positioned, the structural members of the frame can then be bent to conform to the shape of the mandrel. Alternatively, the structural members of the frame can be wound around the mandrel to form the desired configuration. The structural members can then be processed according to the material type used. For example, the structural members can be heat set on the mandrel to set the shape according to techniques as are known.

In an alternative embodiment, different portions of the frame can be formed separately and then joined to form the frame. When the different regions are formed separately, the two portions can be joined by a welding technique, such as laser welding. Other welding or bonding techniques are also possible.

In one embodiment, the structural members of the frame are designed to provide a distribution of forces along the length of the frame. For example, the structural members in the middle region 909 can be designed to provide an expansion force greater than the inlet and outlet regions 905, 913. The distribution of forces can be accomplished in various ways, including changing the spacing between the structural members in the different regions (e.g., the inlet region 905, etc.), changing the number of structural members in the different regions, by heat setting the structural members, or by changing the shape of the frame 902 in the different regions, among others.

As will be appreciated, differing cross-sectional shapes for the structural members are possible, including but not limited to round (e.g., circular, oval, and/or elliptical), rectangular geometries having perpendicular sides, one or more convex sides, or one or more concave sides; semi-circular; triangular; tubular; I-shaped; T-shaped; and trapezoidal. The similarity and/or differences in the cross-sectional geometries and/or cross-sectional dimensions can be based on one or more desired functions to be elicited from each portion of the structural member.

As discussed, natural venous valves partially function via contraction of the calf muscles which compress the veins overlying the bones and direct blood flow toward the heart. Embodiments of the present disclosure, therefore, can be designed to either resist collapsing under the contraction of the muscle, or embodiments can be designed to collapse in a predetermined way while maintaining functionality, as further discussed herein.

In one embodiment, the frame 902 is designed to resist collapsing by providing a sufficient number of structural members in a predetermined configuration so as to resist the prevailing radial pressures. By maintaining a relatively static configuration, the relationship between the valve leaflets 904 and the different regions (e.g., the inlet region 905, the middle region 909, etc.) is controlled. Controlling the relationship between the valve leaflets 904 and the different regions (e.g., the inlet region 905, the middle region 909, etc.) allows the valve leaflets 904 to operate more effectively. For example, by controlling the relationship of the valve leaflets 904 and the different regions (e.g., the inlet region 905, etc.) the size of the valve leaflets 904 can be minimized, thus decreasing the chance that a valve leaflet 904 will come into contact with the frame 902 and/or the native vessel wall.

In an alternative embodiment, the frame 902 can be configured to radially collapse at least partially when the calf muscle contracts over the vein. In one embodiment, the structural members of the frame 902 can be configured to collapse in a predetermined direction so that the valve leaflets 904 are able to shift from the open position to the closed position as illustrated in FIG. 9A when the frame 902 is collapsed. For example, the structural members of the frame 902 can be configured so that when the calf muscle contracts, some of the structural members collapse radially inward in the middle region 909 to compress the sinus region 962. At the same time, other structural members in the middle region 909 radially extend outward so that the attachment locations 936 at the free edges 960 of the valve leaflets 904 are stretched apart. Other configurations are also possible including structural members collapsing in other regions of the frame 902 (e.g., inlet region 905 and outlet region 913) either in combination with the middle region 909 or alone.

The embodiments of the structural member described herein can also be constructed of one or more of a number of materials and in a variety of configurations. The structural member embodiments can have a unitary structure with an open frame configuration. The structural member can also be self-expanding. Examples of self-expanding frames include those formed from temperature-sensitive memory alloy which changes shape at a designated temperature or temperature range, such as Nitinol. Alternatively, the self-expanding structural members can include those having a spring-bias. In addition, the structural member can have a configuration that allows the structural member embodiments be radially expandable through the use of a balloon catheter.

The structural members can be formed from a number of materials. For example, the structural members can be formed from a biocompatible metal, metal alloy, polymeric material, or combination thereof. As described herein, the structural members can be self-expanding or balloon expandable. In addition, as discussed herein, the structural members can be configured so as to have the ability to move radially between the collapsed state and the expanded state. Examples of suitable materials include, but are not limited to, medical grade stainless steel (e.g., 316L), titanium, tantalum, platinum alloys, niobium alloys, cobalt alloys, alginate, or combinations thereof. Additional structural member embodiments may be formed from a shape-memory material, such as shape memory plastics, polymers, and thermoplastic materials. Shape memory alloys having superelastic properties generally made from ratios of nickel and titanium, commonly known as Nitinol, are also possible materials. Other materials are also possible.

The valve can further include one or more radiopaque markers (e.g., rivets, tabs, sleeves, welds). For example, one or more portions of the structural member can be formed from a radiopaque material. Radiopaque markers can be attached to, electroplated, dipped and/or coated onto one or more locations along the frame. Examples of radiopaque material include, but are not limited to, gold, tantalum, and platinum.

The position of the one or more radiopaque markers can be selected so as to provide information on the position, location, and orientation (e.g., axial, directional, and/or clocking position) of the valve during its implantation. For example, radiopaque markers can be configured radially and longitudinally (e.g., around and along portions of the structural members on predetermined portions of the structural members to allow the radial and axial position of the structural members to be determined. So in one embodiment a radiograph image of the structural members taken perpendicular to the valve leaflets in a first clock position can produce a first predetermined radiograph image (e.g., an imaging having the appearance of an inverted "Y") and a radiographic image taken perpendicular to the commissure in a second clock position can produce a second predetermined radiograph image (e.g., an imaging having the appearance of an upright "Y") distinguishable from the first predetermined radiograph image.

Figure 9B:
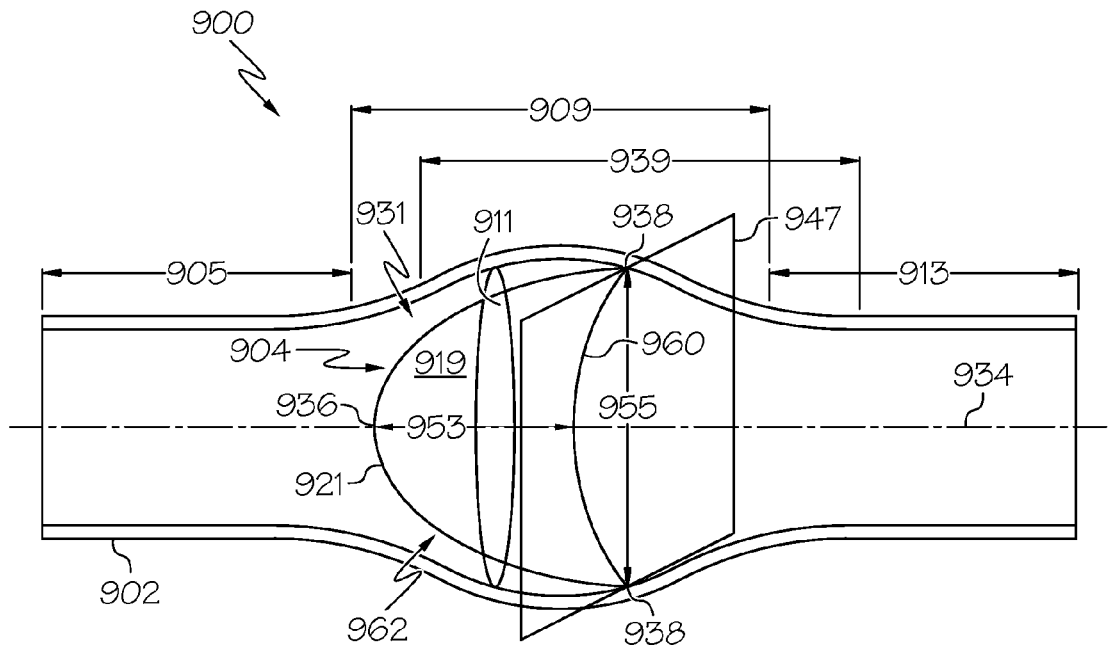
FIG. 9B illustrates an elevation view of a section of the valve illustrated in FIG. 9A.

FIG. 9B is an illustration of a portion of the valve 900 cut along the longitudinal center axis 2-2 in FIG. 9A to show one valve leaflet 904 connected to the frame 902 in the open position, as discussed herein. As illustrated, the frame 902 provides for a center longitudinal center axis 934 extending from the inlet region 905 to the outlet region 913. The center longitudinal center axis 934 provides a reference point to assist in the definition of various features of the valve leaflets 904 in relation to the frame 902 in different regions of the valve (e.g., inlet region 905, middle region 909, etc.).

As discussed herein, the free edge 960 of the valve leaflets 904 can be positioned at a predetermined location 939 along the middle region 909 of the frame 902. For example, as discussed herein, the predetermined location 939 can be positioned approximately at the maximum dimension of the middle cross-sectional area 911. In an additional embodiment, the predetermined location 939 can be positioned at a distance of at least twenty-five (25) percent from the inlet region 905 along the center longitudinal axis 934. For example, the predetermined location 939 can be positioned at a distance ranging from fifty (50) percent from the inlet region 905 to eighty (80) percent from the inlet region 905 along the center longitudinal axis 934. In addition, the predetermined location 939 can be positioned at a distance approximately eighty-five (85) percent from the inlet region 905 along the center longitudinal axis 934. The predetermined location 939 can also be positioned at a distance of greater than one hundred (100) percent from the inlet region 905 along the center longitudinal axis 934. In this embodiment, however, the valve leaflet 904 material must be chosen to resist thrombosis if it comes into contact with the frame 902 or the native vessel wall, as discussed more fully herein. Further, as the predetermined location 939 moves farther from the inlet region 105, the volume 931 of the sinus region 962 decreases, which may affect the backwash, as discussed herein.

The valve leaflet of the present disclosure can be formed of various fluid impermeable, biocompatible materials including synthetic materials or biologic materials. Examples of synthetic materials include, but are not limited to: polyisobutylene-polystyrene (SIBS), polyurethane, poly(dimethylsiloxane) (PDMS), fluoropolymer, proteins, polyethylene terephthalate (PET), protein analogs, copolymers of at least one of these materials, and other biologically stable and tissue-compatible materials as are known in the art. The materials may be formed by spinning, weaving, winding, solvent-forming, thermal forming, chemical forming, deposition, and combinations, include porous coatings, castings, moldings, felts, melds, foams, fibers, microparticles, agglomerations, and combinations thereof.

Possible biologic materials include, but are not limited to, autologous, allogeneic, or xenograft material. These include explanted veins and decellularized basement membrane materials (such as non-crosslinked bladder membrane or amnionic membrane), such as small intestine submucosa (SIS) or umbilical vein. As will be appreciated, blends or mixtures of two or more of the materials provided herein are possible. For example, SIBS could be blended with one or more basement membrane materials.

A material for the valve leaflets can also include a fluid permeable open woven, or knit, physical configuration to allow for tissue in-growth and stabilization, and can have a fluid impermeable physical configuration.

The valve leaflets may also be reinforced with high-strength materials. Examples of high-strength materials are nitinol, stainless steel, titanium, algiloy, elgiloy, carbon, cobalt chromium, other metals or alloys, PET, expanded polytetrafluoroethylene (ePTFE), polyimide, surlyn, and other materials known in the art. The high-strength materials may be in the form of wires, meshes, screens, weaves, braids, windings, coatings, or a combination. The high strength materials may be fabricated by methods such as drawing, winding, braiding, weaving, mechanical cutting, electrical discharge machining (EDM), thermal forming, chemical vapor deposition (CVD), laser cutting, e-beam cutting, chemical forming, and other processes known in the art. One embodiment includes CVD nitinol and wound or braided nitinol.

Suitable bioactive agents which may be incorporated with or utilized together with the valve leaflets may be selected from silver antimicrobial agents, metallic antimicrobial materials, growth factors, cellular migration agents, cellular proliferation agents, anti-coagulant substances, stenosis inhibitors, thrombo-resistant agents, growth hormones, antiviral agents, anti-angiogenic agents, agents, growth hormones, antiviral agents, anti-tumor agents, angiogenic agents, anti-mitotic agents, anti-inflammatory agents, cell cycle regulating agents, genetic agents, cholesterol lowering agents, vasodilating agents, agents that interfere with endogenous vasoactive mechanisms, and hormones, their homologs, derivatives, fragments, pharmaceutical salts thereof, and combinations thereof. Specific examples are discussed herein.

Suitable bioactive agents which may be incorporated with or utilized together with the valve leaflets can also include diagnostic agents or media such as radiologic contrast materials, MRI contrast agents, ultrasound contrast agents, or other imaging aids such as iodinated or non-iodinated contrast media, metallic materials such as gold, iridium, platinum, palladium, barium compounds, gadolinium, encapsulated gas, or silica. Suitable biologically active materials are those than reduce tissue migration, proliferation, and hyperplacia, and include, but are not limited to, the following: paclitaxel, taxotere, rapamycin, sirolimus, and everolimus. Examples of resorbable materials include gelatin, alginate, PGA, PLLA, collagen, fibrin and other proteins. Examples of leakage-reducing materials include ePTFE, hydrophobic coatings, and bioresorbable layers. Materials such as elastin, acellular matrix proteins, decellularized small intestinal submucosa (SIS), and protein analogs, and certain polymers such as PTFE can perform multiple functions such as providing microporous material, leakage-reducing function, bioresorption, and/or facilitation of elution of biologically active material.

To decrease the risk of thrombosis, thrombo-resistant agents associated with the valve leaflets may be selected from the following agents: heparin, heparin sulfate, hirudin, hyaluronic acid, chondroitin sulfate, dermatan sulfate, keratan sulfate, PPack (dextrophenylalanine proline arginine chloromethylketone), lytic agents, including urokinase and streptokinase, including their homologs, analogs, fragments, derivatives and pharmaceutical salts thereof.

Also, anti-coagulants may be selected from the following: D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin, prostaglandin inhibitors, platelet inhibitors, tick antiplatelet peptides and combinations thereof.

In addition, suitable antibiotic agents include, but are not limited to, the following agents: penicillins, cephalosporins, vancomycins, aminoglycosides, quinolones, polymyxins, erythromycins, tetracyclines, chloramphenicols, clindamycins, lincomycins, sulfonamides, their homologs, analogs, derivatives, pharmaceutical salts and combinations thereof.

Anti-proliferative agents include, but are not limited to, the following: enoxaprin, angiopeptin, or monoclonal antibodies capable of blocking smooth muscle cell proliferation, hirudin, acetylsalicylic acid, and combinations thereof.

Useful vascular cell growth inhibitors include, but are not limited to, the following: growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin.

Suitable vascular cell growth promoters include, but are not limited to, transcriptional activators and transcriptional promoters.

Useful anti-tumor agents include, but are not limited to, the following: paclitaxel, docetaxel, taxotere, alkylating agents including mechlorethamine, chlorambucil, cyclophosphamide, melphalan and ifosfamide, antimetabolites including methotrexate, 6-mercaptopurine, 5-fluorouracil and cytarabine, plant alkaloids. including vinblastine, vincristine and etoposide, antibiotics including doxorubicin, daunomycin, bleomycin, and mitomycin, nitrosureas including carmustine and lomustine, inorganic ions including cisplatin, biological response modifiers including interferon, angiostatin agents and endostatin agents, enzymes including asparaginase, and hormones including tamoxifen and flutamide, their homologs, analogs, fragments, derivatives, pharmaceutical salts and combinations thereof.

Furthermore, anti-viral agents include, but are not limited to, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and mixtures thereof.

Useful anti-inflammatory agents include agents such as: dexametbasone, prednisolone, corticosterone, budesonide, estrogen, sulfasalazine, mesalamine, and combinations thereof.

In one embodiment, an anti-mitotic agent may be radioactive material coupled to a biologically compatible carrier. In particular, the radioactive material may be selected from alpha-particle emitting isotopes and beta-particle emitting isotopes. Useful beta-particle emitting isotopes for treatment are generally selected from $^{32}P$, $^{131}I$, $^{90}Y$ and mixtures thereof.

In other embodiments, the bioactive agent(s) associated with the valve leaflets of the present disclosure may be a genetic agent. Examples of genetic agents include DNA, anti-sense DNA, and anti-sense RNA. DNA encoding one of the following may be particularly useful in association with an implantable device according to the present invention: (a) tRNA or rRNA to replace defective or deficient endogenous molecules; (b) angiogenic factors including growth factors such as acidic and basic fibroblast growth factors, vascular endothelial growth factor, epidermal growth factor, transforming growth factor alpha, transforming growth factor beta, platelet-derived endothelial growth factor, platelet-derived growth factor, tumor necrosis factor alpha, hepatocyte growth factor and insulin-like growth factor; (c) cell cycle inhibitors; (d) thymidine kinase and other agents useful for interfering with cell proliferation; and (e) the family of bone morphogenic proteins. Moreover DNA encoding for molecules capable of inducing an upstream or downstream effect of a bone morphogenic protein may be useful.

The valve leaflets may also be treated and/or coated with any number of surface or material treatments. For example, the valve leaflets can be treated with one or more biologically active compounds and/or materials that may promote and/or inhibit endothelization and/or smooth muscle cell growth of the valve leaflets. Examples of such coatings include, but are not limited to, polyglactic acid, poly-L-lactic acid, glycol-compounds, and lipid compounds. Additionally, coatings can include medications, genetic agents, chemical agents, and/or other materials and additives. In addition, agents that limit or decrease cellular proliferation can be useful. Similarly, the valve leaflets may be seeded and covered with cultured tissue cells (e.g., endothelial cells) derived from a either a donor or the host patient which are attached to the valve leaflets. The cultured tissue cells may be initially positioned to extend either partially or fully over the valve leaflets.

Valve leaflets can also be capable of inhibiting thrombus formation. Additionally, valve leaflets may either prevent or facilitate tissue in growth there through, as the particular application for the valve may dictate. For example, valve leaflets on the first outflow surface 921 may be formed from a porous material to facilitate tissue in growth therethrough, while valve leaflets on the first inflow surface 919 may be formed from a material or a treated material which inhibits tissue ingrowth.

In one embodiment, the valve leaflet material chosen can have some dependency on the configuration of the frame. As discussed herein, the frame can be designed to resist collapsing under contraction of the calf muscle. In this embodiment, the material of the valve leaflet can be non-elastic since the frame in the middle region 909 remains approximately the same shape. However, in embodiments where the frame is designed to collapse in a predetermined way under contraction of the muscle, the valve leaflet can be an elastic material so that the valve leaflet attachment locations 936 remain intact while the valve leaflet maintains the ability to shift from the open position to the closed position, as discussed herein. In other embodiments, the elasticity of the valve leaflet material can be dependent on the flexibility of the frame.

In an additional embodiment, the material of the valve leaflets can be sufficiently thin and pliable so as to permit radially-collapsing of the valve leaflets for delivery by catheter to a location within a body lumen, as discussed herein.

FIG. 9B also illustrates the valve 900 of the present disclosure where the valve leaflet 904 has a valve leaflet length 953 and a valve leaflet width 955. The valve leaflet width 955 can be measured between two predetermined locations 938 of the free edge 960 on a plane 947 extending perpendicularly from the center longitudinal axis 934 where the distance is greatest. For the frame shown in FIG. 1A, the free edge 160 of the leaflets 104 extend between the leaflet connections 136 positioned opposite one another on a common axis 144 which is perpendicular to the center longitudinal axis 134. The valve leaflet length 953 can be measured along the inflow surface 919 where the distance between the free edge 960 and an attachment location 936 of the valve leaflet 904 is greatest. For the frame shown in FIG. 1A, the distance from the free edge 160 is greatest from the free edge 160 to the distal point 148 of the predefined portion 146 of the first structural member 112. The valve leaflet length 953 will be discussed more fully herein. In one embodiment, the valve leaflets 904 can have a ratio of valve leaflet length 953 to valve leaflet width 955. For example, the ratio of valve leaflet length 953 to valve leaflet width 955 can range from 0.75:1 to 1.5:1. In another embodiment, the ratio of valve leaflet length 953 to valve leaflet width 955 can be greater than 1.5:1. In an additional embodiment, the ratio of valve leaflet length 953 to valve leaflet width 955 can be less than 0.75:1.

Figure 9C:
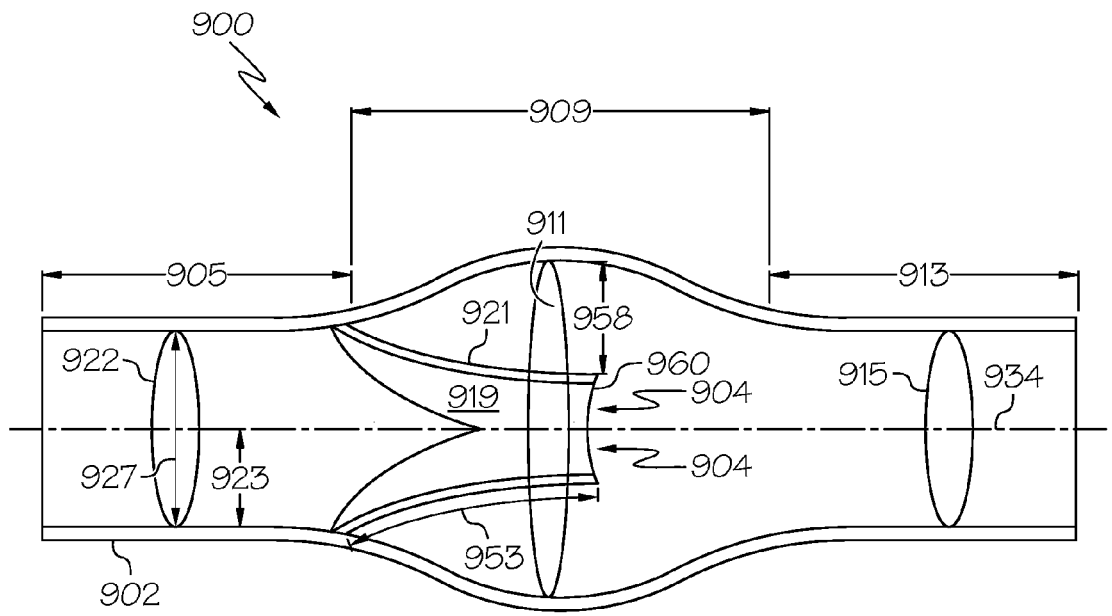
FIG. 9C illustrates a plan view of a section of the valve, specifically the bottom half of the valve illustrated in FIG. 9A.

FIG. 9C is an illustration of a portion of the valve 900 cut along the longitudinal center axis 3-3 in FIG. 9A to show the valve leaflets 904 connected to the frame 902 in the open position, as discussed herein. As discussed herein, specific dimensional relationships for the valve leaflets 904 and the middle region 909 of the frame 902 exist. For example, as illustrated, the valve leaflets 904 in their open configuration define a gap 958 between the free edge 960 of the valve leaflets 904 and the middle region 909 of the frame 902. The gap 958 is measured perpendicular to the center longitudinal axis 934, and in one embodiment, can have a maximum distance from the free edge 960 of the valve leaflets 904 to the middle region 909 of the frame 902 ranging from 0.5 millimeters (mm) to four (4) mm. In an additional embodiment, the gap 958 can have a maximum distance ranging from one (1) to three (3) mm. In yet another embodiment, the gap 958 can have a maximum distance ranging from 1.5 to 2.5 mm. In addition, the distance of the gap 958 between each valve leaflet 904 and the frame 902 can be, but is not necessarily, equal.

In addition to the described maximum distance range of the gap 958, the gap 958 can also be dependent on the inlet diameter 927 of the inlet cross-sectional area 922. In one embodiment, the inlet cross-sectional area 922 can range from six (6) to eighteen (18) millimeters (mm). In an additional embodiment, the inlet cross-sectional area 922 can range from eight (8) to fifteen (15) mm. In yet another embodiment, the inlet cross-sectional area 922 can range from eight (8) to twelve (12) mm.

As discussed herein, the valve leaflets have a first inflow surface 919 and a first outflow surface 921 opposite the inflow surface 919. In addition, as discussed herein, the valve leaflets 904 have a valve leaflet length 953. The valve leaflet length 953 is measured along the inflow surface 919 of the valve leaflet 904 where the distance between the free edge 960 and an attachment location 936 to the frame 902 perpendicular to the free edge 960 in the middle region 909 is greatest. In one embodiment, the valve leaflet length 953 can be configured so that, in the closed position, approximately twenty (20) percent of the inflow surface 919 of the valve leaflets 904 overlap to form a fluid tight commissure.

In one embodiment, the valve leaflet length 953 (L) is be a function of the inlet radius 923 ($r_i$) of the inlet cross-sectional area 922, and can be at least equal to the inlet radius 923 ($r_i$). In another embodiment, the valve leaflet length 953 (L) is a function of the inlet radius 923 ($r_i$), where the function can range from $L=1.2r_i$ to $L=8r_i$. In an additional embodiment, the valve leaflet length 953 (L) is a function of the inlet radius 923 ($r_i$), where the function can range from $L=1.5r_i$ to $L=5r_i$.

Although specific details regarding embodiments of the valve have been discussed in relation to the valve itself, embodiments of the present disclosure can also vary in relation to the size of the body lumen in which the valve is to be placed. For example, in one embodiment, the middle cross-sectional area 911 can be larger than the body lumen cross sectional area and the inlet and outlet cross sectional-areas 922, 915 are approximately equal to the body lumen cross-sectional area. In this embodiment, the middle region 909 will expand the body lumen. In an additional embodiment, the inlet, middle, and outlet cross-sectional areas 922, 911, 915 can be smaller than the body lumen cross-sectional area. Different combinations of cross-sectional area sizes (e.g., inlet cross-sectional area 922, etc.) with respect to the body lumen are also possible.

The valve of the present disclosure has been shown and described in detail including three regions, the inlet region 905, the middle region 909, and the outlet region 913. Additional embodiments of the present disclosure also include a valve with less than three regions. For example, in one embodiment, the frame can be designed to include an inlet region 905 and a middle region 909 such that the middle cross-sectional area 911 is larger than the inlet cross-sectional area 922. In this embodiment, the middle cross-sectional area 911 may be larger than the body lumen cross-sectional area and the inlet cross-sectional area 922 can be approximately equal to the body lumen cross-sectional area, and the valve leaflets 904 extend effectively from the middle region 909 into the body lumen. Other embodiments with more than three regions are also possible.

In addition, different combinations of cross-sectional area sizes (e.g., inlet cross-sectional area 922) with respect to the body lumen are also possible. Further, different combinations of cross-sectional area sizes (e.g., inlet cross-sectional area 922, etc.) with respect to other regions in the valve are also possible.

While the present disclosure has been shown and described in detail above, it will be clear to the person skilled in the art that changes and modifications may be made without departing from the scope of the disclosure. As such, that which is set forth in the foregoing description and accompanying drawings is offered by way of illustration only and not as a limitation. The actual scope of the disclosure is intended to be defined by the following claims, along with the full range of equivalents to which such claims are entitled.

In addition, one of ordinary skill in the art will appreciate upon reading and understanding this disclosure that other variations for the disclosure described herein can be included within the scope of the present disclosure. For example, the frame and/or the valve leaflets can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A valve with ends and a longitudinal length measured from the ends, the valve comprising:
   a frame comprising:
   a first structural member forming an elongate base portion, the first structural member forming two curves at each end of the valve, each end of the valve having only two curves, the elongate base portion including an inlet region that defines an inlet cross sectional area, and an outlet region that defines an outlet cross sectional area, the first structural member defining two valve leaflet connections
   a second structural member extending radially and longitudinally from the first structural member to form a bulbous portion positioned between the ends of the valve, the bulbous portion having a middle cross sectional area,
   the inlet cross sectional area being different than the middle cross sectional area, wherein the bulbous portion has an expansion force that is greater than the inlet region and the outlet region;
   a first valve leaflet and a second valve leaflet, each leaflet engaged to the first structural member,
   each valve leaflet comprising a free edge a first inflow surface, and a first outflow surface opposite the first inflow surface, the free edges extending between the two valve leaflet connections of the first structural member, the free edges of each valve leaflet being configured to shift between an open position and a closed position;

the free edges of the first and second valve leaflets defining a free edge cross sectional area in the open position; and a sinus region defined by a volume between the second structural member at the middle cross sectional area and the first outflow surfaces of the first and second valve leaflets in the open position.

2. The valve of claim 1, where the inlet cross sectional area is approximately equal to the outlet cross sectional area, is greater than the free edge cross sectional area, and is less than the middle cross sectional area.

3. The valve of claim 1, where the middle cross sectional area is greater than the inlet cross sectional and the inlet cross sectional area is greater than the free edge cross sectional area.

4. The valve of claim 1, where the inlet cross sectional area is approximately equal to both the free edge cross sectional area and the outlet cross sectional area, and the inlet cross sectional area is less than the middle cross sectional area.

5. The valve of claim 1, where the inlet cross sectional area is approximately equal to the outlet cross sectional area, the inlet cross sectional area is greater than the middle cross sectional area, and the middle cross sectional area is greater than the free edge cross sectional area.

6. The valve of claim 1, where the frame provides for a longitudinal center axis extending from the inlet region to the outlet region, wherein the free edge of the first and second valve leaflet are at a distance at least twenty-five (25) percent from the inlet region along the longitudinal center axis.

7. The valve of claim 6, where the free edge of the first and second valve leaflet ranges from a distance fifty (50) percent from the inlet region to eighty (80) percent from the inlet region along the longitudinal center axis.

8. The valve of claim 1, where the frame provides for a longitudinal center axis, where the free edge of the first or second valve leaflet in the open position and the bulbous portion of the frame define a gap having a maximum distance ranging from 0.5 to four (4) millimeters (mm) measured perpendicular to the longitudinal center axis.

9. The valve of claim 8, where the gap has a maximum distance ranging from one (1) to three (3) mm.

10. The valve of claim 9, where the maximum distance ranges from 1.5 to 2.5 mm.

11. The valve of claim 1, where the first and second valve leaflets have a valve leaflet length (L) along the inflow surface measured at a greatest length distance between the free edge and an attachment location of the first structural member perpendicular to the free edge, where the inlet cross sectional area has an inlet radius ($r_i$), and where the valve leaflet length (L) is a function of the inlet radius ($r_i$) and is at least approximately equal to the inlet radius ($r_i$).

12. The valve of claim 11, where the valve leaflet length (L) is a function of the inlet radius ($r_i$) that ranges from $L=1.2r_i$ to $L=8r_i$.

13. The valve of claim 12, where the function ranges from $L=1.5r_i$ to $L=5r_i$.

14. The valve of claim 1, where the frame provides for a longitudinal center axis, where the first and second valve leaflets have a valve leaflet width (W) measured at a greatest width distance between locations of the free edge engaged to valve leaflet connections of the first structural member existing on a plane extending perpendicularly from the longitudinal center axis, and where the first and second valve leaflets have a valve leaflet length (L) along the inflow surface measured at a greatest length distance between the free edge and an attachment location of the first structural member perpendicular to the free edge, and the ratio of valve leaflet length (L) to the valve leaflet width (W) ranges from 0.75:1 to 1.5:1.

15. The valve of claim 14, where the ratio of valve leaflet length (L) to valve leaflet width (W) is between 0.75:1 and 1.5:1.

16. The valve of claim 1, where the first valve leaflet is formed of a material selected from the group comprising urinary bladder matrix (UBM), expanded polytetrafluoroethylene (ePTFE), polyurethane, silicone, polystyrene, and a cellurized tissue from a human, an animal, or a plant source.

17. The valve of claim 16, where the first valve leaflet further comprises a metal mesh.

18. The valve of claim 1, the frame maintaining a static configuration when implanted thereby maintaining the relationship between the frame and the first and second leaflets, wherein the first and second leaflets are formed of a non-elastic material.

19. The valve of claim 1, wherein:
the first structural member comprises circumferentially adjacent longitudinal segments, each longitudinal segment extending between a curve at one end of the valve and a curve at the other end of the valve; and
the second structural member comprises bulbous portion members, each bulbous portion member having a first end and a second end, wherein one bulbous portion member engages circumferentially adjacent longitudinal segments of the first structural member, the first end of the bulbous portion member being engaged to one longitudinal segment of the first structural member and the second end of the bulbous portion member being engaged to a circumferentially adjacent longitudinal segment of the first structural member.

20. The valve of claim 1, wherein:
the first structural member forms a first zig-zag ring and a second zig-zag ring interconnected to one another by connecting segments;
the second structural member comprises bulbous portion members engaged to, and extending outward from, the first zig-zag ring to form the bulbous portion;
the first and second leaflets engaged to and extending between the first and second zig-zag rings, with the free edges engaged to the first zig-zag ring.

* * * * *